(12) United States Patent
Li et al.

(10) Patent No.: US 8,652,713 B2
(45) Date of Patent: Feb. 18, 2014

(54) FURAN DERIVATIVE AND ELECTROPHOTOGRAPHIC PHOTOCONDUCTOR

(75) Inventors: Hongguo Li, Shizuoka (JP); Kazukiyo Nagai, Shizuoka (JP); Tetsuro Suzuki, Shizuoka (JP); Yuuji Tanaka, Shizuoka (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 13/394,652

(22) PCT Filed: Sep. 6, 2010

(86) PCT No.: PCT/JP2010/065680
§ 371 (c)(1), (2), (4) Date: Mar. 7, 2012

(87) PCT Pub. No.: WO2011/030881
PCT Pub. Date: Mar. 17, 2011

(65) Prior Publication Data
US 2012/0171601 A1    Jul. 5, 2012

(30) Foreign Application Priority Data

Sep. 11, 2009  (JP) .................................. 2009-210195
Feb. 18, 2010  (JP) .................................. 2010-033286

(51) Int. Cl.
*G03G 15/02*    (2006.01)
*G03G 15/04*    (2006.01)

(52) U.S. Cl.
USPC ........................................ 430/58.75; 430/66

(58) Field of Classification Search
USPC ................................ 430/58.7, 58.75, 59.1, 66
See application file for complete search history.

(56) References Cited

U.S. PATENT DOCUMENTS

| 4,365,961 A | 12/1982 | Weilenmann et al. |
| 5,322,753 A | 6/1994 | Tamura et al. |

(Continued)

FOREIGN PATENT DOCUMENTS

| JP | 5-202135 | 8/1993 |
| JP | 9-278723 | 10/1997 |

(Continued)

OTHER PUBLICATIONS

International Search Report and Written Opinion in PCT/JP2010/065680.

(Continued)

*Primary Examiner* — Stewart Fraser
(74) *Attorney, Agent, or Firm* — Cooper & Dunham LLP

(57) ABSTRACT

A furan derivative represented by the following General Formula (1):

where $Ar_1$ and $Ar_2$ each independently represent an aryl group which may have a substituent, and $R_1$ represents a C1-C6 alkylene group.

6 Claims, 2 Drawing Sheets

(56) References Cited

U.S. PATENT DOCUMENTS

| | | |
|---|---|---|
| 5,488,137 A | 1/1996 | Tamura et al. |
| 5,608,010 A | 3/1997 | Tamura et al. |
| 5,840,454 A | 11/1998 | Nagai et al. |
| 5,882,829 A * | 3/1999 | Hsieh et al. ............ 430/58.15 |
| 6,018,014 A | 1/2000 | Nagai et al. |
| 6,180,303 B1 | 1/2001 | Uematsu et al. |
| 6,416,915 B1 | 7/2002 | Kikuchi et al. |
| 2004/0043312 A1 | 3/2004 | Kikuchi et al. |
| 2004/0242724 A1 | 12/2004 | Saito |
| 2007/0178400 A1 | 8/2007 | Kikuchi et al. |
| 2009/0185821 A1* | 7/2009 | Iwamoto et al. ............ 399/111 |
| 2009/0226828 A1* | 9/2009 | De Jong et al. ............ 430/58.8 |
| 2012/0064444 A1* | 3/2012 | Li et al. ............ 430/66 |

FOREIGN PATENT DOCUMENTS

| | | |
|---|---|---|
| JP | 2000-66424 | 3/2000 |
| JP | 2000-206716 | 7/2000 |
| JP | 3164426 | 3/2001 |
| JP | 3368415 | 11/2002 |
| JP | 3540099 | 4/2004 |
| JP | 2004-231660 | 8/2004 |
| JP | 2006-52190 | 2/2006 |
| JP | 3789008 | 4/2006 |
| JP | 4011790 | 9/2007 |
| JP | 4365961 | 8/2009 |
| JP | 2098912 A1 | 9/2009 |

OTHER PUBLICATIONS

Canary, Stephen A., et al. (1992), "Thermally Reversible Crosslinking of Polystyrene via the Furan-Maleimide Diels-Alder Reaction," Journal of Polymer Science: Part A: Polymer Chemestry, vol. 30, No. 8, pp. 1755-1760.

European search report dated Sep. 14, 2012 in connection with corresponding European patent application No. 10815474.1.

International Search Reaort and Written Opinion in PCT/JP2010/065680.

Canary, Stephen A., et al. (1992), "Thermall Reversible Crosslinking of Polystyrene via the Furan-Maleimide Diels-Alder Reaction," Journal of Polymer Science: Part A: Polymer Chemistry, vol. 30, No. 8, pp. 1755-1760.

Chen, Xiganxu, et al., (2002), "A TeluTrially Re-emendable Cross-linked Polymeric Material," Science , vol. 295, pp. 1698-1702.

Bergman, Sehba D., et al., (2008), "Mendable Polymers," Journal of Material. Chemistry, vol. 18, pp. 41-62.

* cited by examiner

FURAN DERIVATIVE AND ELECTROPHOTOGRAPHIC PHOTOCONDUCTOR

TECHNICAL FIELD

The present invention relates to a novel furan derivative, and to an electrophotographic photoconductor which has a long service life and whose conductive support can be easily recycled.

BACKGROUND ART

In general, electrophotographic photoconductors contain an aluminum drum serving as a conductive support, and a photosensitive layer formed thereon. The photosensitive layer often contains a plurality of layers. In this case, for preventing a lower layer from dissolving in the formation of an upper layer, the lower layer is formed as a three-dimensionally crosslinked cured film in many cases. For example, penetration of a charge generation or transport material into an under layer causes leakage of charges, and thus, the under layer is formed as a film insoluble to a solvent; i.e., a three-dimensionally crosslinked thermosetting resin layer.

Also, conventional electrophotographic photoconductors are consumable supplies which must be replaced due to abrasion over time. In recent years, development has been made on electrophotographic photoconductors which have improved abrasion resistance leading to longer service lives, in attempts to decrease the frequency of replacement and increase the number of sheets printed using one electrophotographic photoconductor to the greatest extent possible. For example, in order to improve the photosensitive layer in mechanical durability, a densely, three-dimensionally crosslinked protective layer is formed on the surface of the photosensitive layer (see, for example, PTLs 1 and 2).

For increasing the mechanical strength or heat resistance of a charge transporting part in electrophotographic photoconductors, a charge transporting material and a binder resin are advantageously combined together as a single material.

Thus, there are proposed a charge transporting monomer formed by introducing a radical polymerizable group into a charge transporting structure and a polymer of the monomer, and an acrylic acid ester having a triphenylamine skeleton and a polymer thereof (see, for example, PTLs 3 and 4).

Also, some patent literatures propose that charge transporting monomers each having two or more radical polymerizable groups are applicable to electrophotographic photoconductors for forming a three-dimensionally crosslinked cured film, and also, propose a variety of such charge transporting monomers. In particular, there are disclosed a number of acrylic acid ester compounds exhibiting excellent crosslinking property, (see, for example, PTLs 5 and 6).

These charge transporting monomers can be used to form a crosslinked charge transporting material having high abrasion resistance. However, they require a polymerization initiator, or irradiation of UV rays or electron beams for crosslinking reaction. Thus, it is unavoidable that the obtained crosslinked charge transporting material is degraded in electrical characteristics.

Furthermore, once conventionally used cured films have a crosslinked structure, they lack thermoplasticity and dissolvability. As a result, these cured films cannot be recycled, and must be disposed of through combustion or landfilling.

Meanwhile, in consideration of resource saving, electrophotographic photoconductors have been increasingly recycled. Especially, attempts have been made to recycling of aluminum drums (i.e., conductive supports). In this case, the photosensitive layers are removed for recycling by generally washing them off with a solvent or peeling them off through swelling. However, the above-described three-dimensionally crosslinked cured, insoluble films on the photoconductors are not swellable or soluble with respect to a solvent, and are quite difficult to remove. Removal of the cured film with a knife or other tools tends to damage the aluminum drum, and even minor scratches prevent the aluminum drum from being recycled.

As described above, electrophotographic photoconductors containing a three-dimensionally crosslinked structure in a photosensitive layer have been increased in recent years, but become difficult to recycle. There is no electrophotographic photoconductor which has such a crosslinked structure and can be easily recycled.

In the meantime, Diels-Alder reaction may proceed in the absence of a catalyst, and is known to a reversible reaction involving a less amount of by-products. There are reports on the synthesis of resins through this reaction (see, for example, PTL 7 and NPL 1). Thus, if a charge transport layer formed through such Diels-Alder reaction can be used in electrophotographic photoconductors, the obtained electrophotographic photoconductors are expected to be excellent in abrasion resistance and charge transportability, and to be easily recycled with less environmental load.

However, such materials and electrophotographic photoconductors have not yet been known.

CITATION LIST

Patent Literature

PTL 1: Japanese Patent Application Laid-Open (JP-A) No. 2000-066424
PTL 2: JP-A No. 2000-206716
PTL 3: JP-A No. 05-202135
PTL 4: JP-A No. 2006-52190
PTL 5: JP-A No. 2000-066424
PTL 6: JP-A No. 2000-206716
PTL 7: JP-A No. 2004-231660

Non Patent Literature

NPL 1: Science, pp. 1698 to 1702 (2002)
NPL 2: J. Mater. Chem., 2008, 18, 41-62
NPL 3: Journal of Polymer Science: Part A: Polymer Chemistry, Vol. 30, 1755-1760, 1992

SUMMARY OF INVENTION

Technical Problem

The present invention aims to solve the above problems pertinent in the art and achieve the following objects. Specifically, an object of the present invention is to provide a furan derivative having excellent charge transportability, participating in Diels-Alder reaction, and being materials for various organic devices. Another object of the present invention is to provide an electrophotographic photoconductor which has a photosensitive layer containing a three-dimensionally crosslinked structure formed for ensuring good coating performance in the production process and which has an excellent recycling property. Still another object of the present invention is to provide an electrophotographic photoconductor which contains a three-dimensionally crosslinked structure formed on a surface of a photosensitive layer, which has excellent abrasion resistance and longer service life, and which has an excellent recycling property.

Solution to Problem

Means for solving the above problems are as follows.

<1> A furan derivative represented by the following General Formula (1):

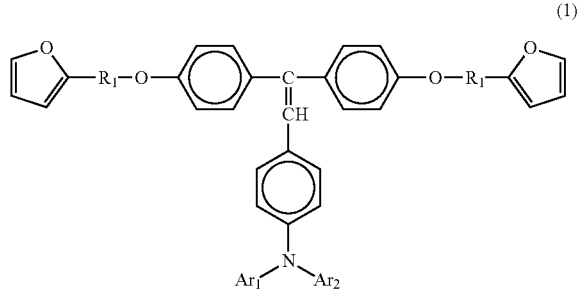

where $Ar_1$ and $Ar_2$ each independently represent an aryl group which may have a substituent, and $R_1$ represents a C1-C6 alkylene group.

<2> The furan derivative according to <1>, wherein the furan derivative is represented by the following General Formula (2):

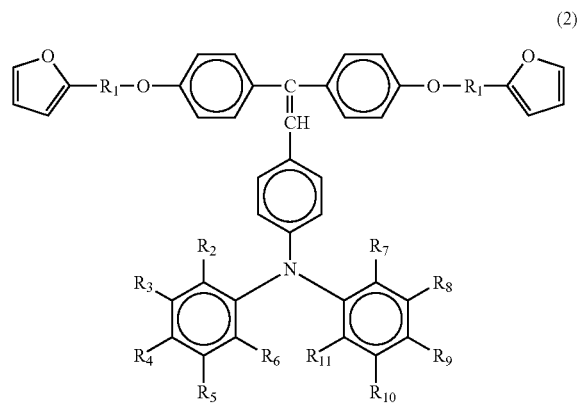

where $R_1$ represents a C1-C6 alkylene group, $R_2$ to $R_{11}$ each independently represent a C1-C6 alkyl group which may have a substituent, a C1-C6 alkoxy group which may have a substituent, or an aryl group which may have a substituent.

<3> The furan derivative according to one of <1> and <2>, wherein the furan derivative is represented by the following General Formula (3):

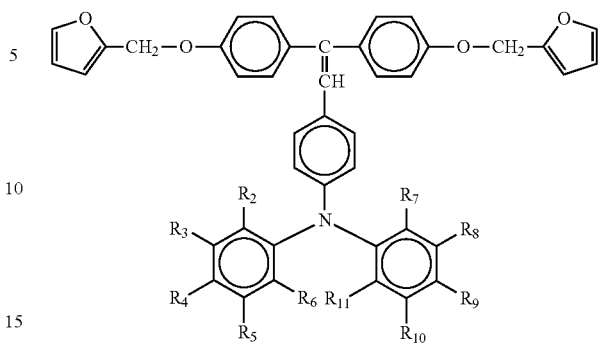

where $R_2$ to $R_{11}$ each independently represent a C1-C6 alkyl group which may have a substituent, a C1-C6 alkoxy group which may have a substituent, or an aryl group which may have a substituent.

<4> An electrophotographic photoconductor including:
a structure three-dimensionally crosslinked through Diels-Alder reaction,
a conductive support, and
a photosensitive layer containing one or more layers, at least the photosensitive layer being provided over the conductive support.

<5> The electrophotographic photoconductor according to <4>, wherein the one or more layers are a charge generation layer and a charge transport layer, wherein at least an under layer, the charge generation layer and the charge transport layer are laminated in this order on the conductive support, and wherein the charge transport layer includes the structure three-dimensionally crosslinked through Diels-Alder reaction.

<6> The electrophotographic photoconductor according to <4>, wherein the one or more layers are a charge generation layer and a charge transport layer, wherein at least an under layer, the charge generation layer, the charge transport layer and a protective layer are laminated in this order on the conductive support, and wherein the protective layer includes the structure three-dimensionally crosslinked through Diels-Alder reaction.

<7> The electrophotographic photoconductor according to any one of <4> to <6>, wherein the structure three-dimensionally crosslinked through Diels-Alder reaction is formed through Diels-Alder reaction between a furan derivative serving as a diene and a maleimide derivative serving as a dienophile.

<8> The electrophotographic photoconductor according to <7>, wherein the furan derivative contains a triarylamine partial structure.

<9> The electrophotographic photoconductor according to one of <7> and <8>, wherein the furan derivative is represented by the following General Formula (1):

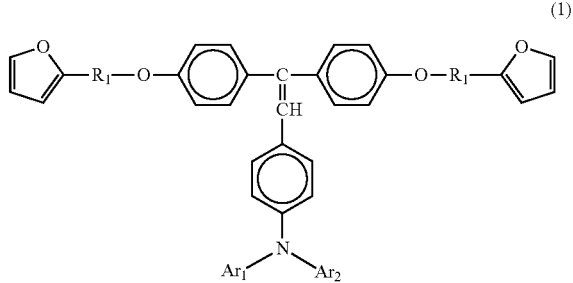

(1)

where $Ar_1$ and $Ar_2$ each independently represent an aryl group which may have a substituent, and $R_1$ represents a C1-C6 alkylene group.

<10> The electrophotographic photoconductor according to any one of <7> to <9>, wherein the furan derivative is represented by the following General Formula (2):

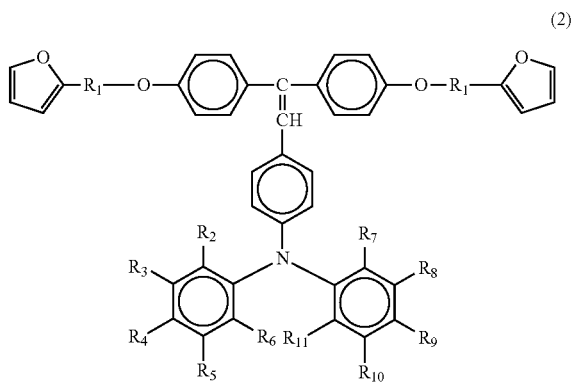

(2)

where $R_1$ represents a C1-C6 alkylene group, $R_2$ to $R_{11}$ each independently represent a C1-C6 alkyl group which may have a substituent, a C1-C6 alkoxy group which may have a substituent, or an aryl group which may have a substituent.

<11> The electrophotographic photoconductor according to any one of <7> to <10>, wherein the furan derivative is represented by the following General Formula (3):

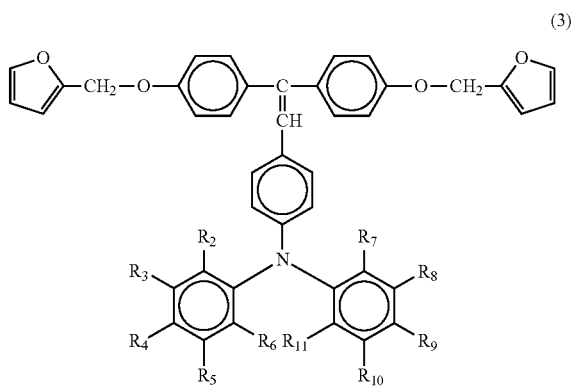

(3)

where $R_2$ to $R_{11}$ each independently represent a C1-C6 alkyl group which may have a substituent, a C1-C6 alkoxy group which may have a substituent, or an aryl group which may have a substituent.

<12> The electrophotographic photoconductor according to any one of <7> to <11>, wherein the maleimide derivative contains three or more maleimide functional groups.

Advantageous Effects of Invention

The furan derivative of the present invention is a novel compound which has both reactivity and charge transportability (hole transportability), and can form through Diels-Alder reaction a thermoplastic resin or crosslinked cured resin. The obtained resin shows charge transportability, and thus, is useful in semiconductor materials for organic devices such as organic EL elements, organic electrophotographic photoconductors, organic TFTs and organic solar cells.

The electrophotographic photoconductor of the present invention is formed through Diels-Alder reaction. Even when unreacted diene and dienophile groups remain, these groups have low polarity and thus do not cause failure in chargeability. In addition, Diels-Alder reaction requires no catalyst, and thus there exist no adverse side effects caused by the catalyst. Therefore, the electrophotographic photoconductor has excellent intrinsic characteristics, and, through three-dimensional crosslinking reaction, has high mechanical characteristics and insolubility to a solvent.

In one embodiment of the electrophotographic photoconductor of the present invention, the photosensitive layer contains a three-dimensionally crosslinked structure formed through Diels-Alder reaction. Thus, in a recycle step, the crosslinking bonds decompose through retro-Diels-Alder reaction. As a result, the polymer is converted into low-molecular-weight monomers which are readily dissolved in a solvent, and thus, the photosensitive layer of the electrophotographic photoconductor can be readily removed, which is remarkably advantageous.

DESCRIPTION OF EMBODIMENTS (Furan Derivative)

Figure 1:
FIG. 1 is a schematic view of one example of a layer structure of an electrophotographic photoconductor of the present invention.

Diels-Alder reaction is a reaction between a diene and a dienophile, and can be conducted between various compounds. Since electrical characteristics are degraded to a less extent and the reaction temperature is lower, combination of a furan derivative (diene) and a polyfunctional maleimide (dienophile) is most suitable for materials of organic devices including organic photoconductors. In particular, from the viewpoint of obtaining reactivity and hole transportability, it has been found that the furan derivative is advantageously used as a hole transporting compound exhibiting electron donating property. In view of this, the present invention provides furan derivatives represented by General Formulas (1), (2) and (3) as a suitable furan derivative having excellent Diels-Alder reactivity and hole transportability.

In General Formulas (1), (2) and (3), $R_1$ represents a C1-C6 alkylene group, and is preferably a methylene group.

Each of $Ar_1$ and $Ar_2$ is an aryl group which may have a substituent. Examples of the aryl group which may have a substituent include phenyl, naphthyl, biphenylyl, terphenylyl, pyrenyl, fluorenyl, 9,9-dimethyl-2-fluorenyl, azulenyl, anthryl, triphenylenyl, chrysenyl and groups represented by General Formulas (4), (5), (6) and (7).

(4)

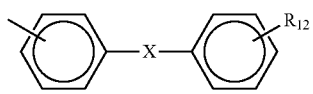
(5)

In General Formula (5), X represents —O—, —S—, —SO—, —SO$_2$—, —CO—, a divalent group represented by the following General Formula (6) or a divalent group represented by the following General Formula (7); and $R_{12}$ represents a hydrogen atom, a halogen atom, an alkyl group which may have a substituent, or an aryl group which may have a substituent.

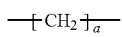
(6)

In General Formula (6), a is an integer of 1 to 12.

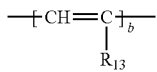
(7)

In General Formula (7), $R_{13}$ represents a hydrogen atom, a halogen atom, an alkyl group which may have a substituent, or an aryl group which may have a substituent; and b is an integer of 1 to 3.

Examples of the substituent include halogen atoms, C1-C6 alkyl groups which may have a substituent, and alkoxy groups which may have a substituent.

Examples of the halogen atom include a fluorine atom, a chlorine atom, a bromine atom and an iodine atom.

Examples of the substituent the C1-C6 alkyl groups have include halogen atoms and a phenyl group.

Examples of the alkoxy group which may have a substituent include alkoxy groups having the above C1-C6 alkyl groups which may have a substituent. Specific examples include methoxy, ethoxy, n-propoxy, i-propoxy, t-butoxy, n-butoxy and benzoxy.

$R_2$ to $R_{11}$ each independently represent a C1-C6 alkyl group which may have a substituent, an alkoxy group which may have a substituent, or an aryl group which may have a substituent. Examples of the substituent the C1-C6 alkyl group has include halogen atoms and a phenyl group.

Examples of the C1-C6 alkyl group which may have a substituent include methyl, ethyl, n-propyl, i-propyl, t-butyl, s-butyl, n-butyl, i-butyl, n-pentyl, n-hexyl, cyclohexyl, trifluoromethyl, benzyl, 4-chlorobenzyl and 4-methylbenzyl.

Examples of the alkoxy group which may have a substituent include alkoxy groups having the above C1-C6 alkyl groups which may have a substituent. Specific examples include methoxy, ethoxy, n-propoxy, i-propoxy, t-butoxy, n-butoxy and benzoxy.

Examples of the aryl group include phenyl, naphthyl, biphenylyl, terphenylyl, pyrenyl, fluorenyl, 9,9-dimethyl-2-fluorenyl, azulenyl, anthryl, triphenylenyl and chrysenyl.

Examples of the substituent include halogen atoms and C1-C6 alkyl groups. Specifically, the halogen atoms and the C1-C6 alkyl groups are exemplified as described above.

Specific examples of the furan derivative will be given below.

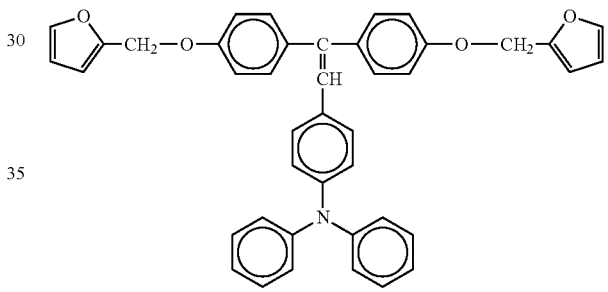
No. 1

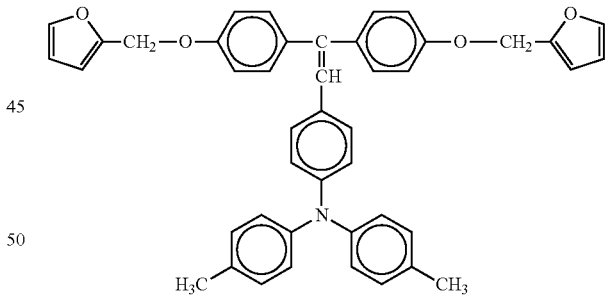
No. 2

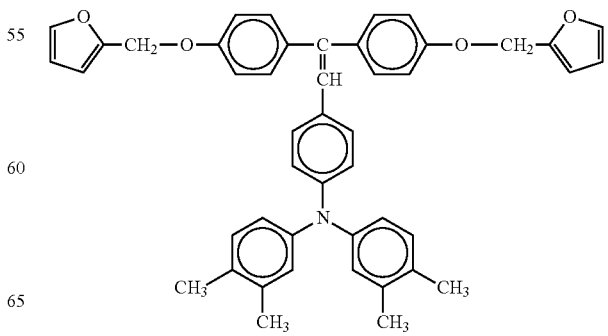
No. 3

No. 4
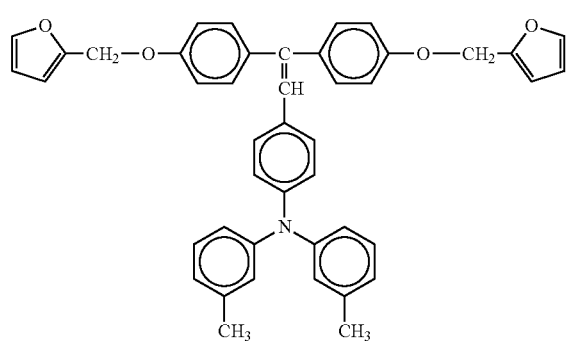
No. 8
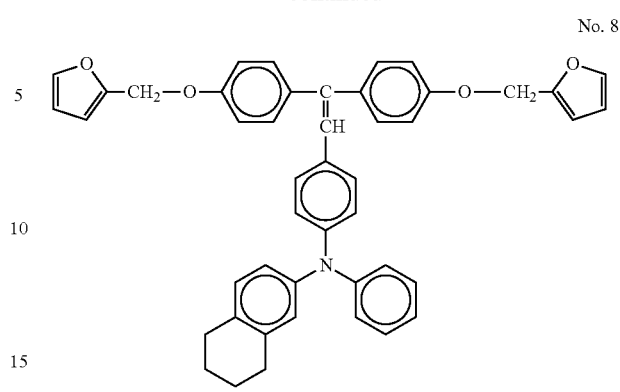
No. 5
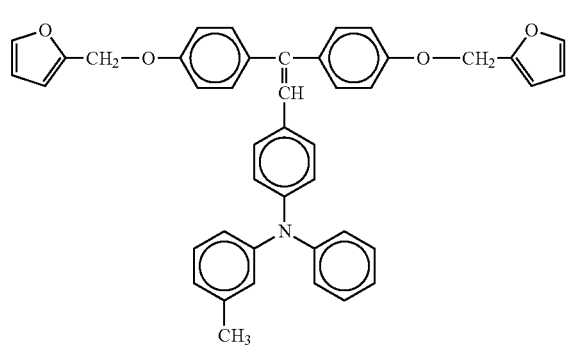
No. 9
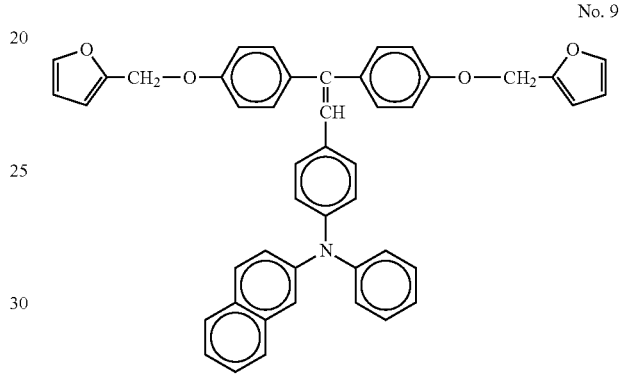
No. 6
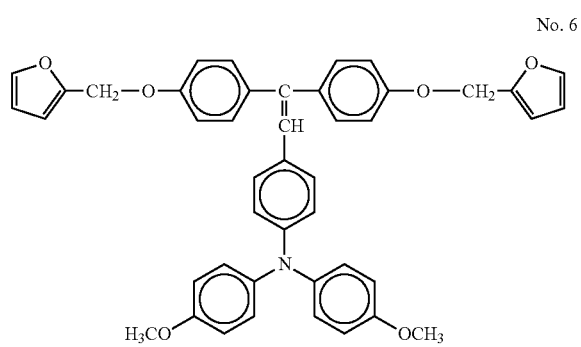
No. 10
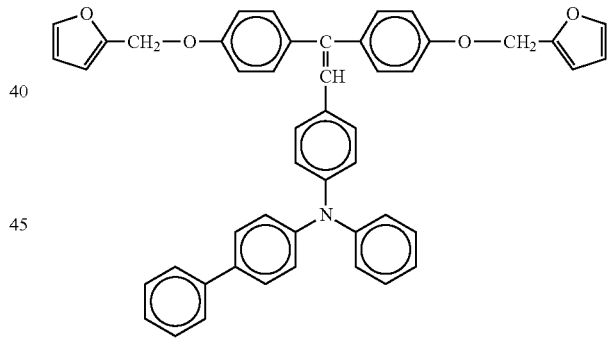
No. 7
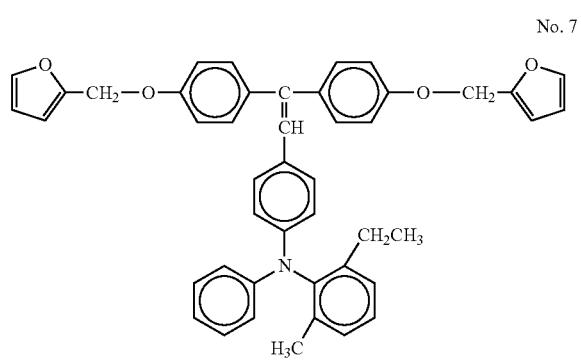
No. 11
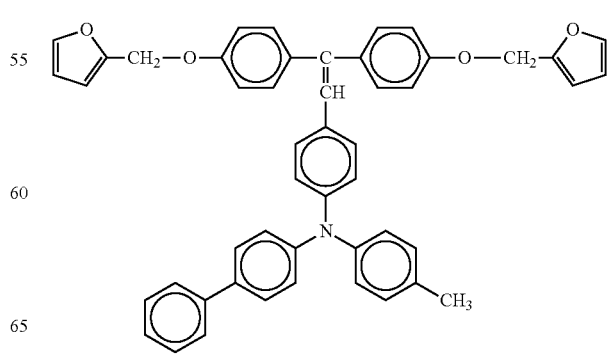

No. 12
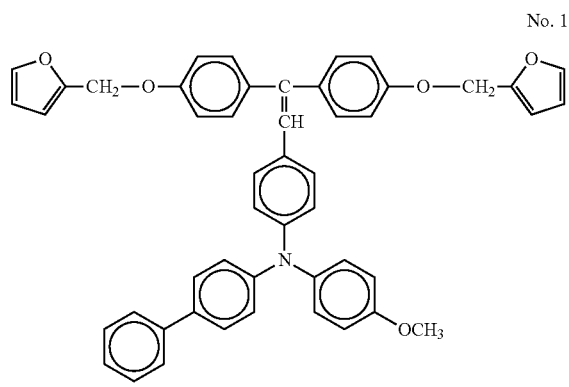

No. 13
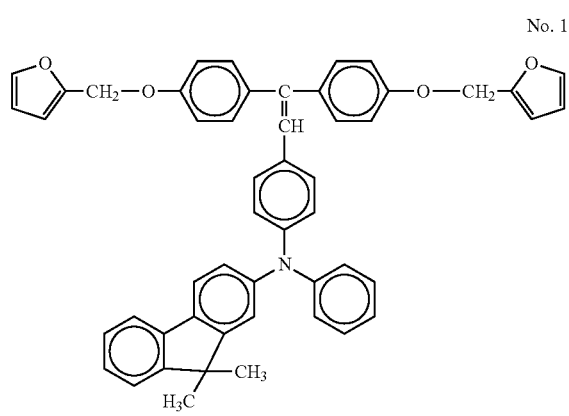

No. 14
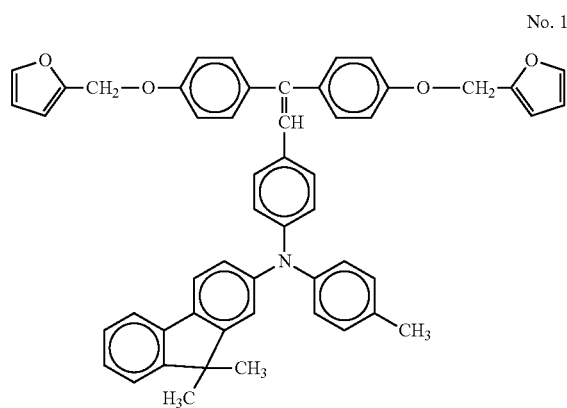

No. 15
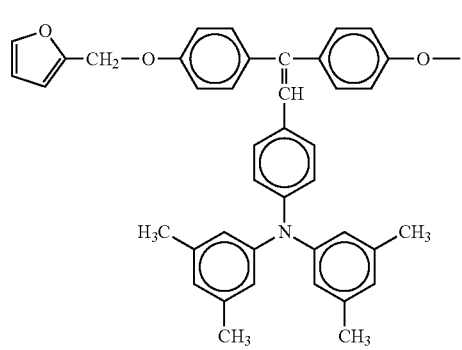

No. 16
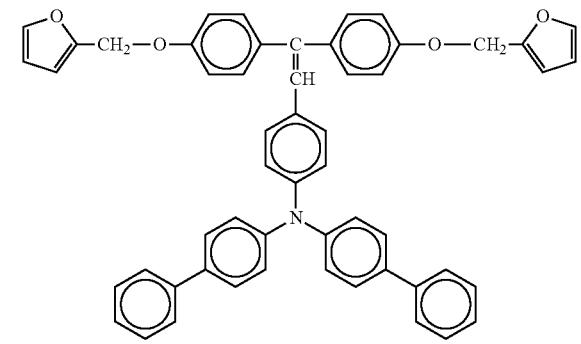

No. 17
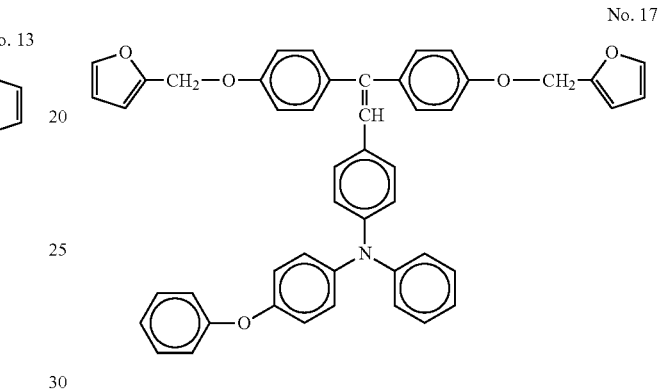

The furan derivative of the present invention is a novel compound, and can be easily synthesized through the following Mitsunobu reaction, for example.

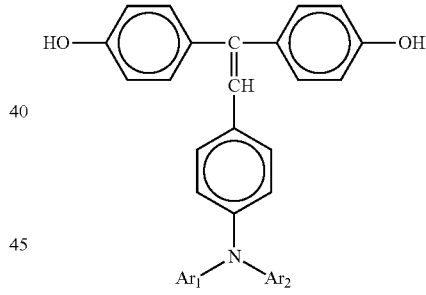

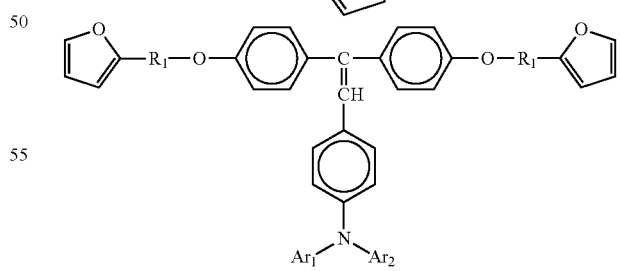

For example, the furan derivative can be produced through dehydrocondensation between an alcohol compound and a diphenol derivative in the presence of triphenylphosphine and an azodicarboxylic acid ester serving as a catalyst.

Here, both the azodicarboxylic acid ester and the triphenylphosphine may be commercially available products.

Examples of the azodicarboxylic acid ester include 1,1'-(azodicarbonyl)dipiperidine, tert-butyl azodicarboxylate, dibenzyl azodicarboxylate, diethyl azodicarboxylate, diisopropyl azodicarboxylate and dimethyl azodicarboxylate.

Examples of the triphenylphosphine include 4-(dimethylamino)phenyldiphenylphosphine, dicyclohexylphenylphosphine, diethylphenylphosphine, diphenyl-2-pyridylphosphine, isopropyldiphenylphosphine, phenoxydiphenylphosphine, tri-n-octylphosphine, tri-tert-butylphosphine, tributylphosphine, tricyclohexylphosphine, tri-n-hexylphosphine and triphenylphosphine.

The alcohol compound usable is an alcohol represented by the following General Formula (8).

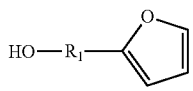

General Formula (8)

In General Formula (8), $R_1$ has the same meaning as defined in General Formulas (1), (2) and (3).

Examples of the alcohol represented by General Formula (8) include furfuryl alcohol. The alcohol may be a commercially available product or a synthetic product.

The diphenol derivative usable is a diphenol derivative represented by the following General Formula (9).

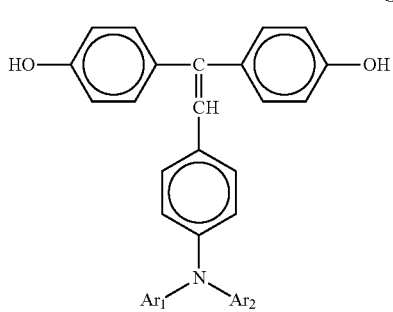

General Formula (9)

In General Formula (9), $Ar_1$ and $Ar_2$ have the same meanings as defined in General Formulas (1), (2) and (3).

The diphenol derivative represented by General Formula (9) can be synthesized by a conventionally known method described in, for example, Japanese Patent (JP-B) No. 3540099.

Examples of the solvent usable include pyridine, triethylamine, tetrahydrofuran, dimethylformamide, diethyl ether, dimethylsulfoxide, dichloromethane, chloroform and toluene.

The reaction temperature is, for example, −5° C. to the boiling point of the solvent, preferably 0° C. to room temperature.

The reaction is preferably performed under flow of inert gas such as nitrogen and argon.

The reaction is generally completed for 1 hour to 24 hours.
(Electrophotographic Photoconductor)

An electrophotographic photoconductor of the present invention includes a conductive support and a photosensitive layer containing one or more layers (i.e., a single-layered or multi-layered photosensitive layer). The electrophotographic photoconductor contains a structure three-dimensionally crosslinked through Diels-Alder reaction.

<Diels-Alder Reaction>

Next, Diels-Alder reaction will be described.

The basic reaction of Diels-Alder reaction is a cycloaddition reaction between 1,3-butadiene (diene compound (diene)) and ethylene (parent diene compound (dienophile)) (formation of 6-membered hydroxyl ring). As has been known, this reaction is facilitated when the diene has an electron-donating group as a substituent and the dienophile has an electron-attracting group as a substituent.

The diene or dienophile usable in Diels-Alder reaction is not particularly limited. From the viewpoint of facilitating the reaction, the following structures are exemplified as preferred dienes and dienophiles.

—Preferred Diene Structure—

Cyclopentadiene, cyclohexadiene, furan, and compounds having them as a substituent —Preferred Dienophile Structure—

Cyanoethylene, dimethyl maleate, maleic anhydride, maleic acid imide, vinyl methyl ketone, diethylacetylene dicarboxylate, and compounds having them as a substituent Conventionally known materials may be used as the above dienes and dienophiles.

In particular, combinational use of a furan derivative serving as diene (i.e., a compound having a furan structure(s)) and a maleimide derivative serving as dienophile (i.e., a compound having a maleic acid imide structure(s)) shows good Diels-Alder reactivity at a temperature of 110° C. or lower. The furan derivative and the maleimide derivative can form a structure stably maintained under usage conditions of the photoconductor (−5° C. to 60° C.). Also, these can decompose their crosslinking bonds as a result of retro-Diels-Alder reaction which rapidly occurs with heating to a relatively low temperature of 110° C. to 150° C. For this reason, combinational use of them is most preferred.

Diels-Alder reaction can proceed at room temperature to 100° C.

Diels-Alder reaction is known to accelerate by the addition of, for example, a Lewis acid. Thus, the Lewis acid may be added to the reaction system in such an amount that an electrophotographic photoconductor is not adversely affected.

Examples of the Lewis acid include those conventionally known in the art such as aluminum chloride, titanium chloride, tin chloride and lithium perchlorate.

The cycloaddition product obtained through Diels-Alder reaction may be a stereoisomer (such as an exo or endo form) depending on the combination of diene and dienophile, but whichever can be used. For example, when furan and maleic anhydride are allowed to react through Diels-Alder reaction at a temperature higher than 20° C., the resultant cycloaddition product is mainly an exo form which is thermodynamically stable. In the present invention, heat is applied for allowing Diels-Alder reaction to proceed, since such manner is advantageous in terms of productivity. Thus, the obtained crosslinked structure may be formed mainly of exo-form cycloaddition products.

As described above, Diels-Alder reaction is a reaction which forms a 6-membered addition product from diene and dienophile. This reaction requires no catalyst such as an acid or a base, and can proceed only by the application of heat (even at room temperature). Furthermore, the obtained addition product is stable.

In conventional electrophotographic photoconductors containing a thermosetting resin, the thermosetting resin contains highly polar functional groups such as an OH group, an NCO group and an SiOH group, and thus, the residual groups thereof reduce electrical resistance of the photosensitive layer, leading to failure in chargeability thereof. When epoxy or acrylic curing reaction is employed, it is necessary to add an acid catalyst, a base catalyst, a radical polymerizable initiator, etc. These reagents cause adverse side effects in characteristics of the photoconductor, such as decrease in chargeability and generation of residual potential, which is problematic.

In contrast, in the case of the electrophotographic photoconductor of the present invention which is formed through a three-dimensional crosslinking reaction by Diels-Alder reaction, even when unreacted diene group and dienophile group remain, these groups have low polarity and thus do not cause failure in chargeability. In addition, Diels-Alder reaction requires no catalyst, and thus there exist no adverse side effects caused by the catalyst. Therefore, the obtained electrophotographic photoconductor has excellent intrinsic characteristics, and, through three-dimensional crosslinking reaction, has high mechanical characteristics and insolubility to a solvent.

Also, Diels-Alder reaction is known to be a reversible reaction. Thus, a polymer obtained through this reaction decomposes through retro-Diels-Alder reaction simply by the application of heat.

Therefore, when the electrophotographic photoconductor of the present invention whose photosensitive layer contains a three-dimensionally crosslinked structure formed through Diels-Alder reaction is thermally treated in a recycle step, the crosslinking bonds decompose through retro-Diels-Alder reaction. As a result, the polymer is converted into low-molecular-weight monomers which are readily dissolved in a solvent, and thus, the photosensitive layer of the electrophotographic photoconductor can be readily removed, which is remarkably advantageous.

<Structure Three-dimensionally Crosslinked Through Diels-Alder Reaction>

The structure three-dimensionally crosslinked through Diels-Alder reaction refers to a structure obtained through Diels-Alder reaction from a compound having two or more diene structures in one molecule thereof and a compound having two or more dienophile structures in one molecule thereof (when the number of diene structures in one molecule is two, the number of dienophile structures in one molecule is preferably three).

In the electrophotographic photoconductor including a conductive support, an under layer and a photosensitive layer containing a charge generation layer and a charge transport layer, at least the under layer, the charge generation layer and the charge transport layer being laminated in this order on the conductive support, when the above structure three-dimensionally crosslinked through Diels-Alder reaction is used in the charge transport layer of the electrophotographic photoconductor, the structure three-dimensionally crosslinked through Diels-Alder reaction is formed by, for example, the following methods.

The charge transport layer generally contains a low-molecular-weight charge transporting compound and a binder resin.

Thus, two diene structures are introduced into one molecule of the low-molecular-weight charge transporting compound conventionally known and a plurality of dienophile structures are introduced into the binder resin, and then the obtained products may be thermally cured to form the structure three-dimensionally crosslinked through Diels-Alder reaction.

Also, a monomer having three or more dienophile structures, instead of the binder resin, and the low-molecular-weight charge transporting compound into which the diene structures have been introduced may be cured to form the structure three-dimensionally crosslinked through Diels-Alder reaction.

In addition, the dienophile structures are introduced into the low-molecular-weight charge transporting compound and the diene structures are introduced into the binder resin or monomer, and then the obtained products may be cured to form the structure three-dimensionally crosslinked through Diels-Alder reaction.

Furthermore, the low-molecular-weight charge transporting compound is used without any treatment, and a monomer or oligomer having a plurality of diene structures and a monomer or oligomer having a plurality of dienophile structures may be allowed to react through Diels-Alder reaction to form a binder resin of the structure three-dimensionally crosslinked through Diels-Alder reaction.

The reaction temperature at which Diels-Alder reaction is performed is preferably 40° C. to 110° C. When the reaction temperature is in excess of 110° C., retro-Diels-Alder reaction may predominantly occur. When the reaction temperature is lower than 40° C., Diels-Alder reaction does not sufficiently proceed and the solvent may disadvantageously remains. The reaction temperature is most preferably 60° C. to 110° C.

In the case where the electrophotographic photoconductor, containing the structure three-dimensionally crosslinked through Diels-Alder reaction, is a negatively-charged laminate photoconductor in which the low-molecular-weight charge transporting compound is a compound exhibiting hole transportability and having a triarylamine structure, the low-molecular-weight charge transporting compound is preferably a diene derivative, more preferably a furan derivative, since it has an electron-donating property in view of the structure thereof.

The triarylamine structure refers to a tertiary amine structure in which three aryl groups are bonded to nitrogen. Examples of the aryl groups include phenyl, naphthyl, fluorenyl, biphenylyl, anthryl and pyrenyl.

Also, in the electrophotographic photoconductor including a conductive support, an under layer, a charge generation layer, a charge transport layer and a protective layer, at least the under layer, the charge generation layer, the charge transport layer and the protective layer being laminated in this order on the conductive support, when the above structure three-dimensionally crosslinked through Diels-Alder reaction is used in the protective layer of the electrophotographic photoconductor, the above description regarding the use in the charge transport layer also applies.

When used in the under layer, the structure three-dimensionally crosslinked through Diels-Alder reaction is formed by, for example, the following methods.

In general, the under layer mostly contains a thermosetting resin (e.g., melamine resins and urethane resins) and conductive microparticles dispersed therein (e.g., titanium oxide and tin oxide). Thus, the thermosetting resin may be replaced with a resin formed through Diels-Alder reaction. The resin formed through Diels-Alder reaction may be formed using conventionally known resin compositions. The resin formed through Diels-Alder reaction is, for example, resins and resin-forming compositions described in, for example, NPL 2 (J. Mater. Chem., 2008, 18, 41-62) (schemes 2 and 3, FIGS. 1 and 2, and scheme 4). Also, there can be employed resins and synthesis methods described in NPL 3 (Journal of Polymer Science: Part A: Polymer Chemistry, Vol. 30, 1755-1760, 1992).

Also in the single-layered electrophotographic photoconductor including a conductive support and a single photosensitive layer in which a charge generating pigment and one or more charge transporting compounds are dispersed in a binder resin, the structure three-dimensionally crosslinked through Diels-Alder reaction can be used similar to the case where the structure three-dimensionally crosslinked through Diels-Alder reaction is used in the charge transport layer of the multi-layered photosensitive layer.

Tables 1-1 to 1-6 list specific examples of the diene used for forming the structure three-dimensionally crosslinked through Diels-Alder reaction. In these tables, the compounds or structures referred to by A-1 to A-7 and (1)-No. 1 to (1)-No. 17 (A-14 to A-30) are charge transport compounds into which a diene group has been introduced. In particular, the compounds referred to by (1)-No. 1 to (1)-No. 17 (A-14 to A-30) are furan derivatives represented by General Formulas (1) to (3). Also, in the tables, the compounds referred to by A-10 to A-12 are random copolymers whose compositional ratio is n/m.

TABLE 1-1

| No. | Structure |
|---|---|
| A-1 | 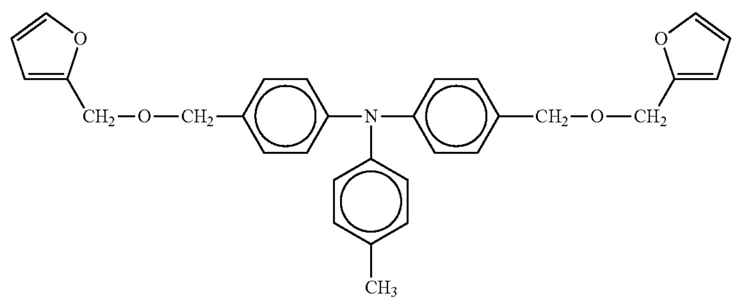 |
| A-2 | 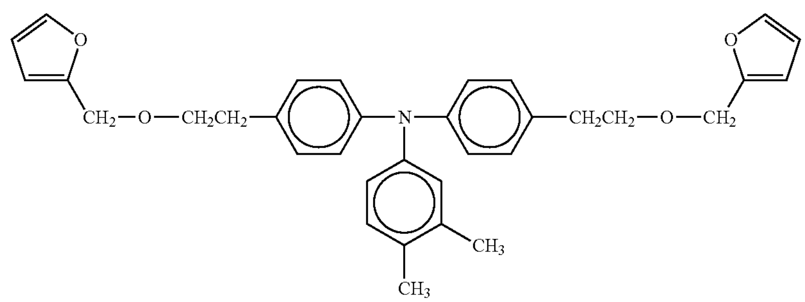 |
| A-3 | 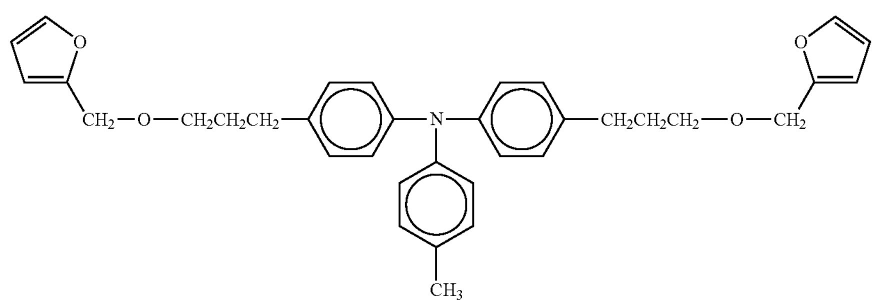 |
| A-4 | 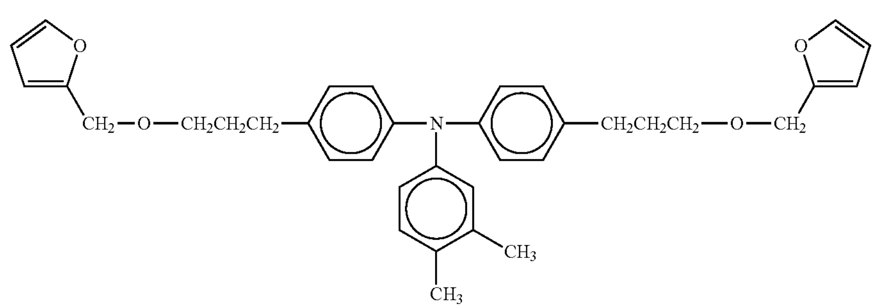 |

TABLE 1-1-continued
| No. | Structure |
|---|---|
| A-5 | 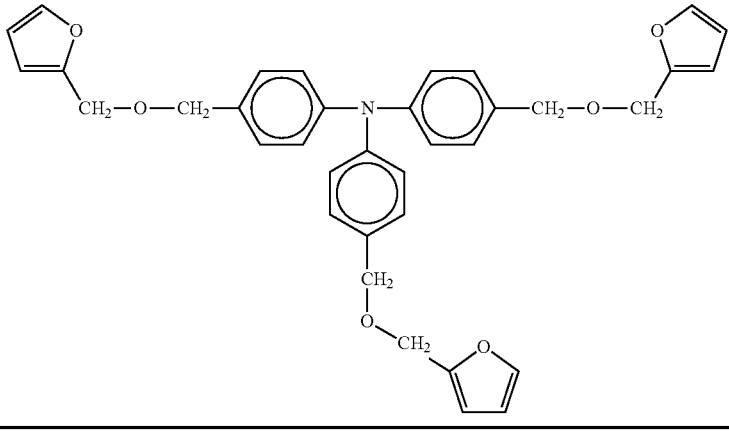 |
TABLE 1-2
| No. | Structure |
|---|---|
| A-6 | 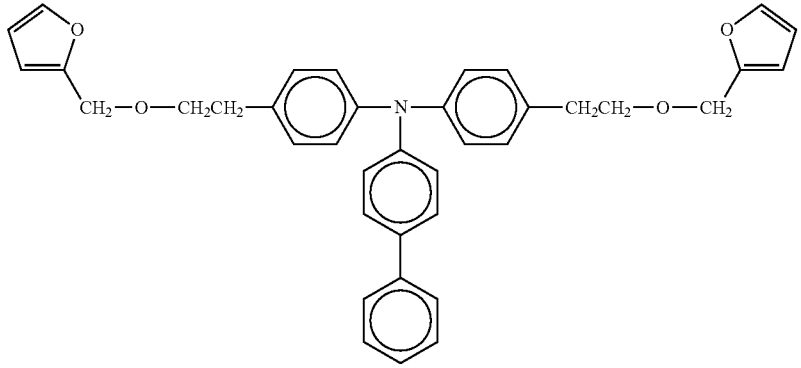 |
| A-7 | 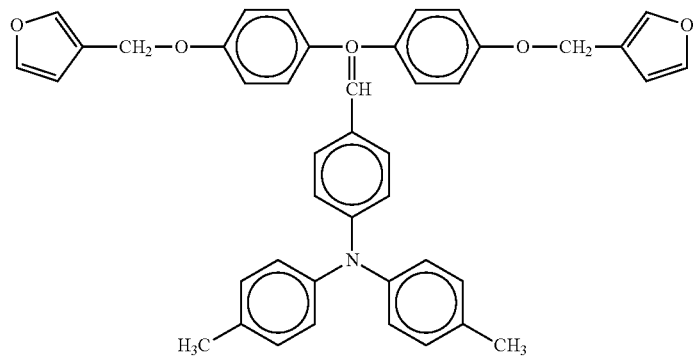 |
| A-8 | 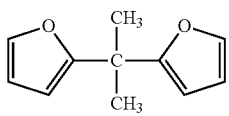 |
| A-9 | 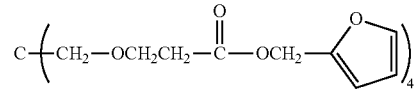 |

TABLE 1-2-continued
| No. | Structure |
|---|---|
| A-10 | $\left[ (-CH_2-CH-)_{n'}/(-CH_2-CH-)_m \right]_{20}$ with phenyl and p-(CH₂-O-CH₂-furan) substituents |
TABLE 1-3
| No. | Structure |
|---|---|
| A-11 | $\left[ (-CH_2-CH-)_{n'}/(-CH_2-C(CH_3)-)_m \right]$ with C(=O)-O-(CH₂)₅-CH₃ and C(=O)-O-CH₂-furan substituents |
| A-12 | $\left[ (-CH_2-CH-)_{n'}/(-CH_2-C(CH_3)-)_m \right]$ with phenyl and C(=O)-O-CH₂-furan substituents |
| A-13 | 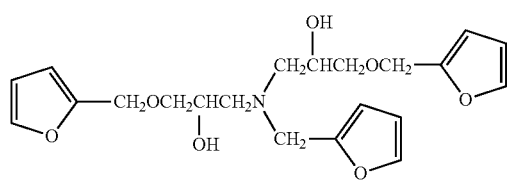 |

TABLE 1-3-continued

| No. | Structure |
|---|---|
| (1)-No. 1 (A-14) | Furfuryl-CH₂-O-C₆H₄-C(=CH-C₆H₄-N(C₆H₅)₂)-C₆H₄-O-CH₂-Furfuryl |
| (1)-No. 2 (A-15) | Furfuryl-CH₂-O-C₆H₄-C(=CH-C₆H₄-N(p-tolyl)₂)-C₆H₄-O-CH₂-Furfuryl |

TABLE 1-4

| No. | Structure |
|---|---|
| (1)-No. 3 (A-16) | Furfuryl-CH₂-O-C₆H₄-C(=CH-C₆H₄-N(3,4-dimethylphenyl)₂)-C₆H₄-O-CH₂-Furfuryl |

TABLE 1-4-continued

| No. | Structure |
|---|---|
| (1)-No. 4 (A-17) | 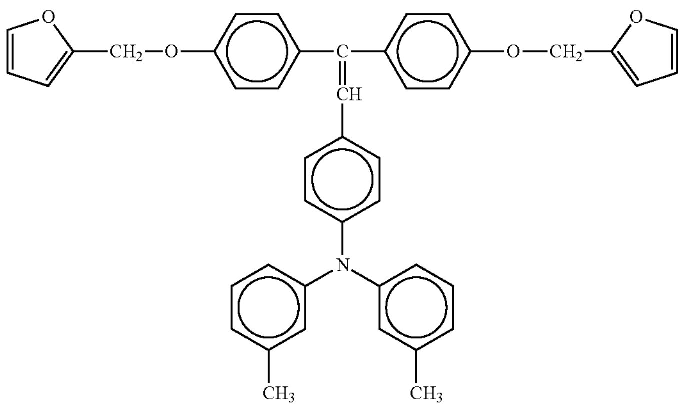 |
| (1)-No. 5 (A-18) | 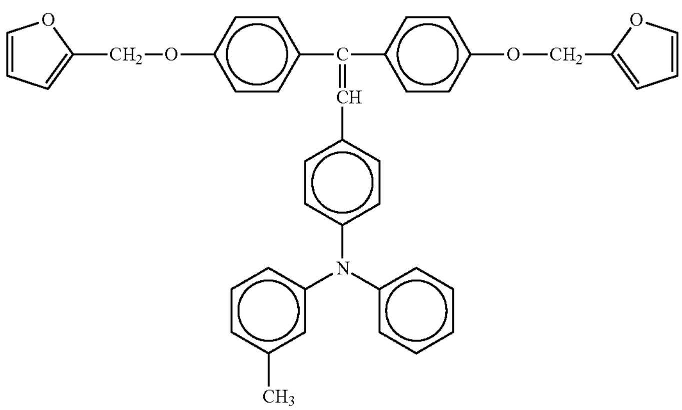 |
| (1)-No. 6 (A-19) | 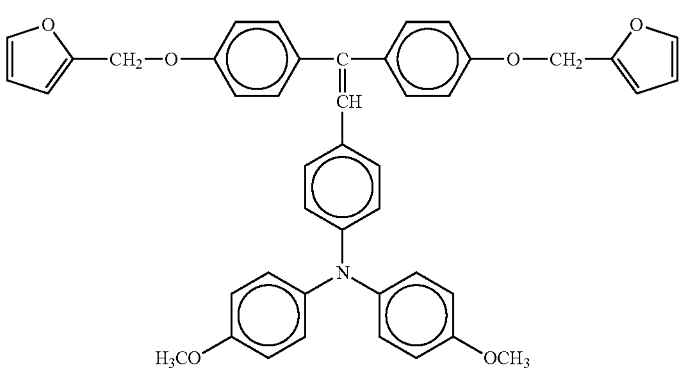 |
| (1)-No. 7 (A-20) | 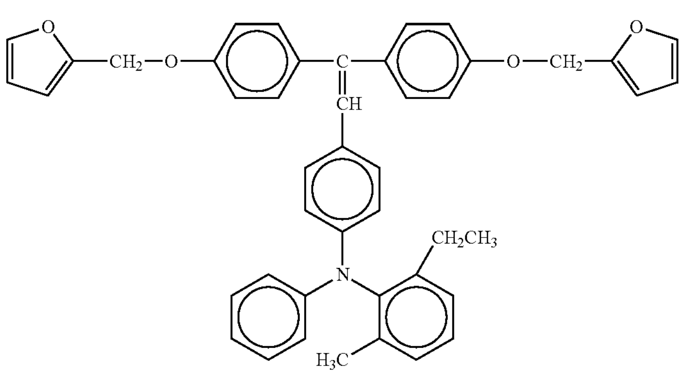 |

TABLE 1-5

| No. | Structure |
|---|---|
| (1)-No. 8 (A-21) | 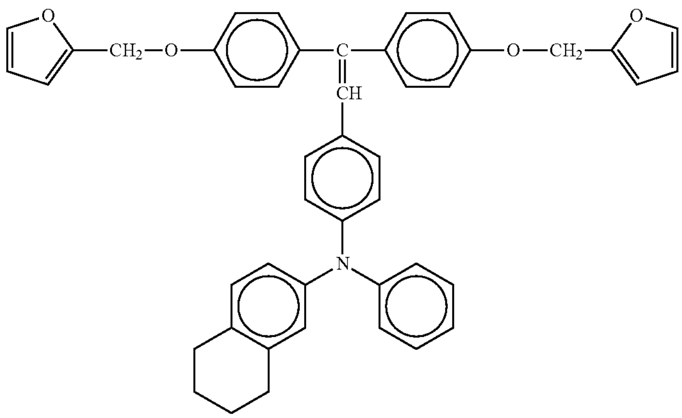 |
| (1)-No. 9 (A-22) | 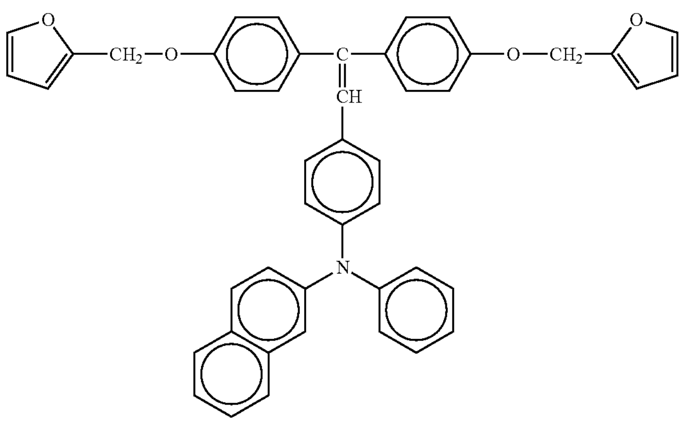 |
| (1)-No. 10 (A-23) | 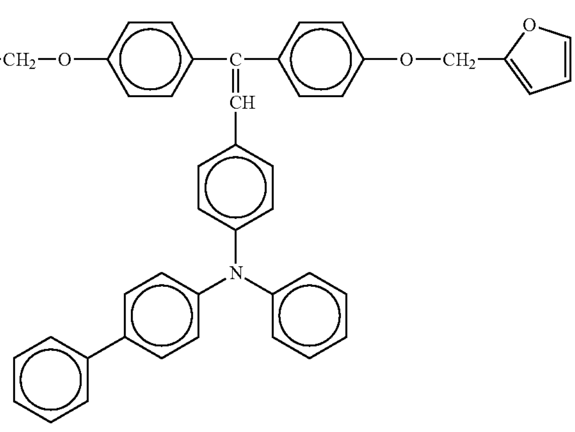 |

TABLE 1-5-continued

| No. | Structure |
|---|---|
| (1)-No. 11 (A-24) | Structure with furan-CH₂-O-phenyl groups connected to central C=CH, with phenyl-N(biphenyl)(tolyl) amine |
| (1)-No. 12 (A-25) | Structure with furan-CH₂-O-phenyl groups connected to central C=CH, with phenyl-N(biphenyl)(4-methoxyphenyl) amine |

TABLE 1-6

| No. | Structure |
|---|---|
| (1)-No. 13 (A-26) | Structure with furan-CH₂-O-phenyl groups connected to central C=CH, with phenyl-N(phenyl)(9,9-dimethylfluorenyl) amine |

TABLE 1-6-continued

| No. | Structure |
|---|---|
| (1)-No. 14 (A-27) | *(chemical structure)* |
| (1)-No. 15 (A-28) | *(chemical structure)* |
| (1)-No. 16 (A-29) | *(chemical structure)* |

TABLE 1-6-continued

| No. | Structure |
|---|---|
| (1)-No. 17 (A-30) | (structure shown) |

Tables 2-1 and 2-2 list specific examples of the dienophile suitably used for forming the structure three-dimensionally crosslinked through Diels-Alder reaction. The compound referred to by B-1 is a charge transporting compound into which a dienophile group has been introduced. In the tables, the compound referred to by B-8 is a random copolymer whose compositional ratio is n/m.

TABLE 2-1

| No. | Structure |
|---|---|
| B-1 | (structure shown) |
| B-2 | 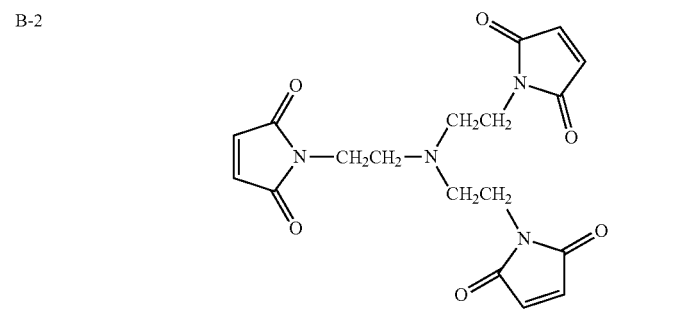 |
| B-3 | 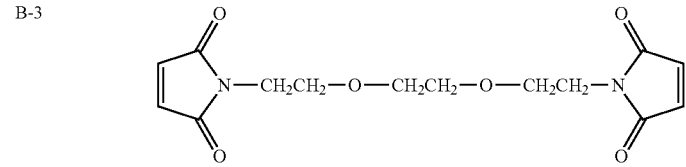 |

TABLE 2-1-continued

| No. | Structure |
|-----|-----------|
| B-4 | (structure: bismaleimide with diphenylmethane) |
| B-5 | (structure: bismaleimide with disiloxane linker) |

TABLE 2-2

| No. | Structure |
|-----|-----------|
| B-6 | (structure: bismaleimide with tetrasiloxane linker) |
| B-7 | (structure: N,N'-ethylene-bismaleimide) |

TABLE 2-2-continued

| No. | Structure |
|-----|-----------|
| B-8 | $\left[ (-CH_2-CH-)_n / (-CH_2-CH-)_m \right]$ with phenyl and 4-(maleimidomethyl)phenyl pendant groups |

These dienes and dienophiles can be obtained by a conventionally known method. Among the dienes and dienophiles listed in the above tables, the furan derivatives having a triphenylamine partial structure are novel compounds and synthesized through conventionally known reaction.

For example, the furan derivatives represented by General Formulas (1) to (3) can be readily synthesized through the synthesis reaction described above in relation to the furan derivative of the present invention.

In Compound Nos. A1 to A6, as shown in the following reaction scheme, the furan groups can be introduced via ether bonds formed through Williamson reaction between a haloalkyl group-containing triphenylamine compound and an alkoxide derived from furfuryl alcohol.

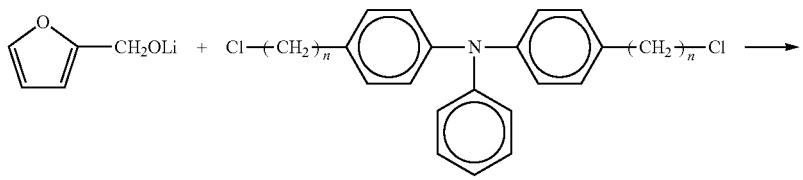

-continued

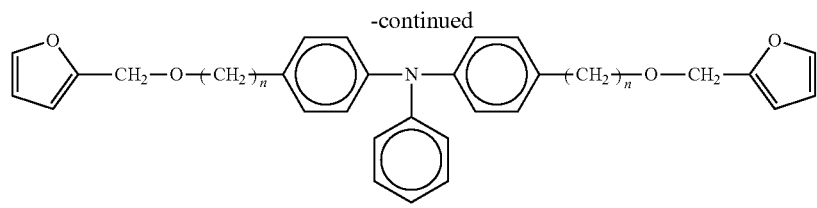

In addition, as shown in the following reaction scheme, the diene group (furan group) can be introduced through addition condensation reaction between an isocyanate and an alcohol or through esterification between an acid chloride and an alcohol.

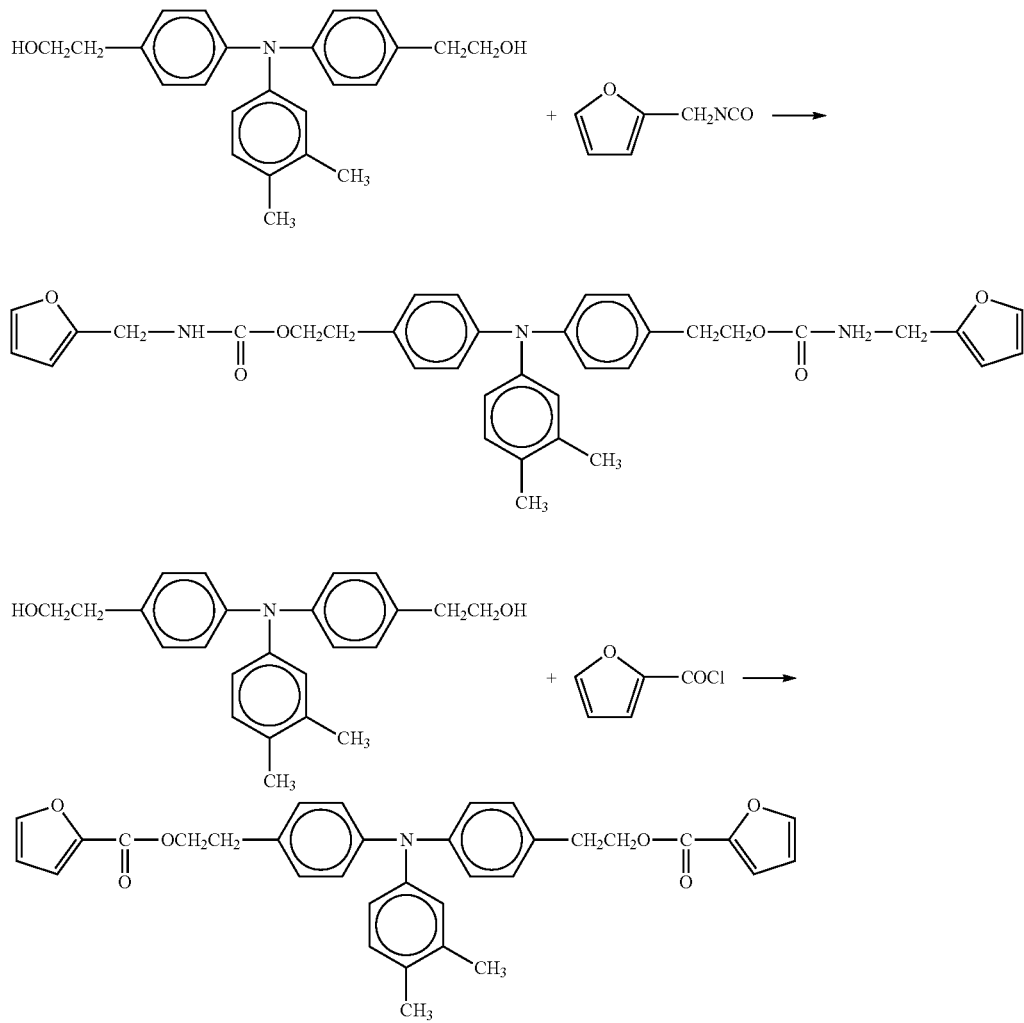

Furthermore, as shown in the following reaction scheme, Compound No. B1 can be produced by imidizing a diamino compound and maleic anhydride in the presence of an acid catalyst.

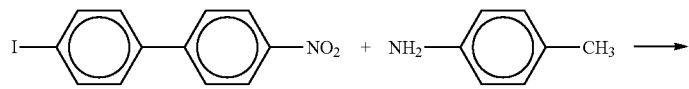

-continued

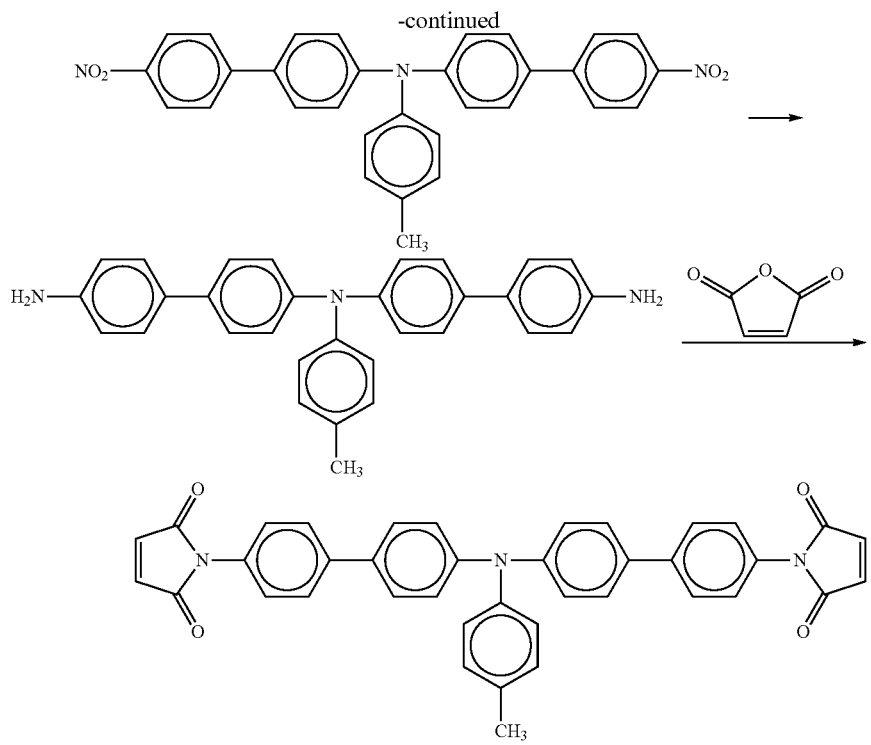

In this manner, by introducing a structure serving as diene or dienophile into conventionally known charge transporting compounds through various reactions, dienes or dienophiles having various charge transporting properties can be produced. The thus-produced dienes or dienophiles can be used to form the structure three-dimensionally crosslinked through Diels-Alder reaction.

Next, referring to FIGS. 1 to 5, description will be given with respect to the layer structure of the electrophotographic photoconductor of the present invention. Each of FIGS. 1 to 5 is a cross-sectional view of the electrophotographic photoconductor. In these figures, reference numeral 10 denotes a conductive support, reference numeral 11 an under layer, reference numeral 12 a charge generation layer, reference numeral 13 a charge transport layer, reference numeral 14 a protective layer, reference numeral 20 a single-layered photosensitive layer containing a charge generating compound and a charge transporting compound, and reference numeral 21 a protective layer for the single-layered photosensitive layer.

FIG. 1 illustrates a layer structure of the most basic laminate photoconductor, in which the charge generation layer 12 and the charge transport layer 13 are sequentially laminated on the conductive support 10. When the laminate photoconductor is negatively charged in use, a charge transporting compound having hole transportability is used in the charge transport layer. When the laminate photoconductor is positively charged in use, a charge transporting compound having electron transportability is used in the charge transport layer.

In the electrophotographic photoconductor illustrated in FIG. 1, the structure three-dimensionally crosslinked through Diels-Alder reaction is mainly applied to the charge transport layer 13. The charge generation layer 12 is generally formed as a very thin pigment dispersion layer which is insoluble to a solvent, and thus, is not often formed as a three-dimensionally crosslinked film. Therefore, there is low need to apply to the charge generation layer the structure three-dimensionally crosslinked through Diels-Alder reaction, but the structure can be used instead of a resin serving as a dispersion medium for a pigment.

Figure 2:
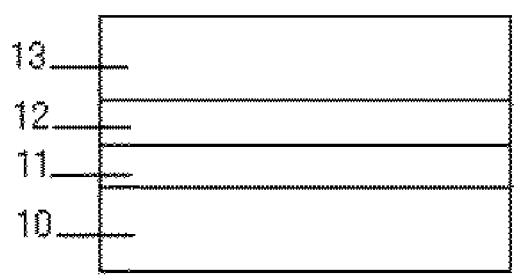
FIG. 2 is a schematic view of another example of a layer structure of an electrophotographic photoconductor of the present invention.

FIG. 2 illustrates a layer structure of the above basic laminate photoconductor further including the under layer 11, and the photoconductors having this layer structure are most practically used. The structure three-dimensionally crosslinked through Diels-Alder reaction is mainly applied to the charge transport layer 13 and the under layer 11. Similar to the above description regarding the electrophotographic photoconductor illustrated in FIG. 1, there is low need to apply to the charge generation layer 12 the structure three-dimensionally crosslinked through Diels-Alder reaction.

Figure 3:
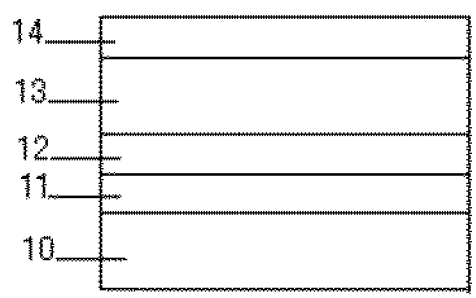
FIG. 3 is a schematic view of still another example of a layer structure of an electrophotographic photoconductor of the present invention.

FIG. 3 illustrates a layer structure further including the protective layer 14 at the uppermost surface of the photoconductor. Commonly used electrophotographic photoconductors often have a protective layer having high mechanical strength for preventing degradation due to charging or abrasion caused by a cleaning blade. The protective layer contains an inorganic filler, is formed of a sol-gel thermosetting resin, or is formed of an acrylic curable resin crosslinked by electron beams or UV rays. In the present invention, the structure three-dimensionally crosslinked through Diels-Alder reaction can be applied to the protective layer, and the obtained protective layer can be excellent in both mechanical characteristics and photoconductor characteristics.

Figure 4:
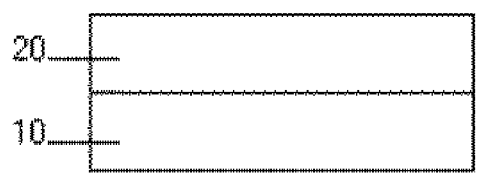
FIG. 4 is a schematic view of yet another example of a layer structure of an electrophotographic photoconductor of the present invention.

FIG. 4 illustrates a layer structure composed of the conductive support 10 and the photosensitive layer 20 mainly containing a charge transporting compound. The structure three-dimensionally crosslinked through Diels-Alder reaction can be applied to the photosensitive layer 20.

Figure 5:
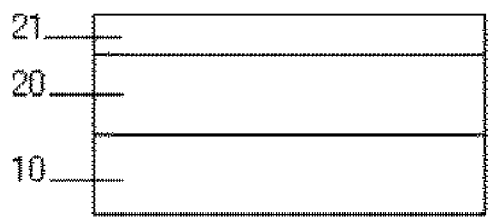
FIG. 5 is a schematic view of even another example of a layer structure of an electrophotographic photoconductor of the present invention.

FIG. 5 illustrates a layer structure further including the protective layer 22 on the single-layered photosensitive layer 20. Similar to the case of the protective layer 14, the structure three-dimensionally crosslinked through Diels-Alder reaction can be applied to the protective layer 22, and the obtained protective layer can be excellent in both mechanical characteristics and photoconductor characteristics.

The composition of each of these layers may be those conventionally known in the art, except for the layer to which the structure three-dimensionally crosslinked through Diels-Alder reaction is applied.

EXAMPLES

The present invention will next be described by way of Examples, which should not be construed as limiting the present invention thereto. In the following Examples and Comparative Examples, the unit "part(s)" is "part(s) by mass" unless otherwise specified.

Example 1

A reaction container equipped with a stirrer, a thermometer and a dropping funnel was charged with a diphenol derivative having the following Chemical Formula (10 g), furfuryl alcohol (4.06 g, product of TOKYO CHEMICAL INDUSTRIES Co., Ltd.), tributylphosphine (10.05 g, product of TOKYO CHEMICAL INDUSTRIES Co., Ltd.) and dehydrated dichloromethane (200 mL). Separately, 1,1'-(azodicarbonyl) dipiperidine (12.53 g, product of TOKYO CHEMICAL INDUSTRIES Co., Ltd.) was dissolved in dichloromethane. Under nitrogen flow, the resultant dichloromethane solution (30 mL) was slowly added dropwise to the reaction container at 3° C. The mixture was allowed to react at the same temperature for 10 hours. Thereafter, the reaction mixture was filtrated, and the reaction solvent was removed with an evaporator, to thereby obtain yellow powder as a crude product. In addition, the thus-obtained yellow powder was purified using a silica gel column, to thereby obtain 4.53 g of a furan derivative (Compound No. 2) as pale yellow powder.

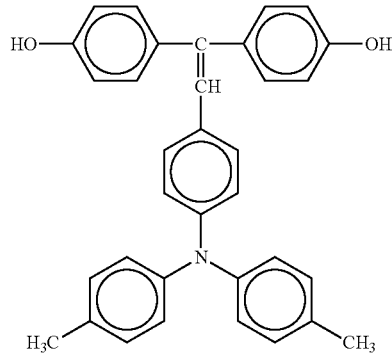

The obtained furan derivative was subjected to elemental analysis using a fully automatic elemental analyzer vario MicroCube (product of Elementar, Germany). The results of the elemental analysis are shown below.

| | Elemental Analysis (%) | | |
| --- | --- | --- | --- |
| | C | H | N |
| Found: | 81.85% | 5.80% | 1.96% |
| Calculated: | 82.09% | 5.79% | 2.18% |

Figure 6:
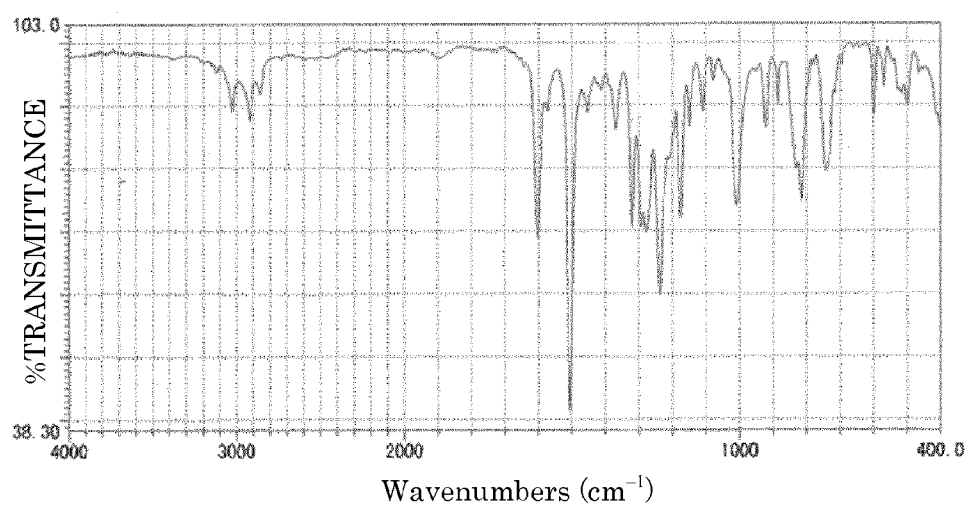
FIG. 6 is an infrared absorption spectrum chart (obtained by the KBr tablet method) of the furan derivative obtained in Example 1.

Also, the furan derivative was measured for infrared absorption spectrum using a Fourier transform infrared spectrometer FT-720 (product of HORIBA, Ltd.). The thus-measured infrared absorption spectrum (the KBr tablet method) was shown in FIG. 6.

Example 2

A polyamide resin (CM-8000, product of TORAY INDUSTRIES, INC.) was dissolved in a methanol/butanol solvent mixture. The resultant solution was applied onto an aluminum plate with a doctor blade, and naturally dried to form an intermediate layer of 0.3 μm. Separately, a bisazo compound having the following Chemical Formula (serving as a charge generating compound) was milled in a cyclohexanone/2-butanone solvent mixture with a ball mill. The resultant dispersion liquid was applied onto the intermediate layer with a doctor blade, and naturally dried to form a charge generation layer having a thickness of 0.5 μm.

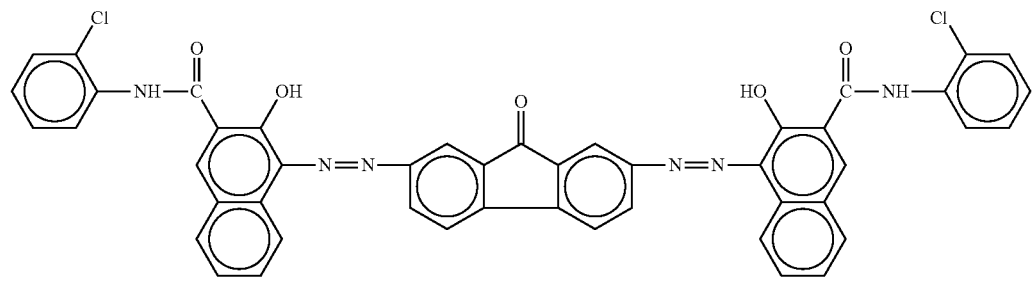

Next, a charge transport layer coating liquid having the following composition was applied onto the above-formed charge generation layer with a doctor blade, and naturally dried. Then, the resultant layer was dried at 130° C. for 30 min to form a charge transport layer having a thickness of 20 nm. Through the above procedure, an electrophotographic photoconductor was produced.

[Charge Transport Layer Coating Liquid]

Furan derivative obtained in Example 1 (Compound No. 2): 1.75 parts

Polycarbonate resin (PANLITE TS2050, product of Teijin Chemical Co., Ltd.): 2.5 parts Tetrahydrofuran: 24.1 parts Using a commercially available electrostatic copying paper analyzer (Model SP428, product of Kawaguchi Electric Works Ltd.), the obtained electrophotographic photoconductor was charged in the dark through corona discharging at −6 kV for 20 sec, and then was measured for surface potential $V_m$ (V). In addition, after left to stand for 20 sec in the dark, the electrophotographic photoconductor was measured for surface potential $V_0$ (V). Next, the electrophotographic photoconductor was irradiated with light from a tungsten lamp so that the illuminance on the surface thereof was adjusted to 5.3 lux. Then, the time (sec) required that the $V_0$ decreased to ½ thereof was measured, and the exposure dose $E_{1/2}$ (lux·sec) was calculated. The results are shown below.

$V_m$=−1,360 V $V_0$=−1,079 V $E_{1/2}$32 1.15 lux·sec

From the above values, it was confirmed that the furan derivative of the present invention had excellent electrical characteristics and could be used as a charge transporting material.

Example 3

Similar to Example 2, an intermediate layer and a charge generation layer were formed on an aluminum plate. Next, a charge transport layer coating liquid having the following composition was applied onto with a doctor blade, and then naturally dried. The resultant layer was dried at 80° C. for 8 hours to form a charge transport layer having a thickness of 17 μm. Through the above procedure, a photoconductor was produced.

[Charge Transport Layer Coating Liquid]

Furan derivative obtained in Example 1 (Compound No. 2): 3 parts 2,2-Di(2-furyl)propane (product of TOKYO CHEMICAL INDUSTRIES Co., Ltd.): 0.9 parts Trismaleimide having the following Structural Formula (obtained according to NPL 1): 2.4 parts Dichloromethane: 25.2 parts

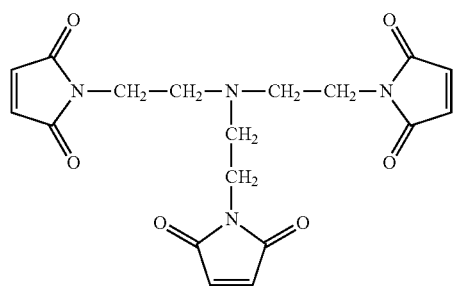 [SMILES: O=C1C=CC(=O)N1CCN(CCN1C(=O)C=CC1=O)CCN1C(=O)C=CC1=O]

Similar to Example 2, the obtained photoconductor was evaluated for electrical characteristics. The results are shown below.

$V_m$=−1,067 V $V_0$=−920 V $E_{1/2}$=1.68 lux·sec

Example 4

The charge transport layer coating liquid used in Example 3 was applied onto a glass slide with a doctor blade, and naturally dried. The resultant layer was dried at 80° C. for 8 hours to form a film having a thickness of 17 μm. Using a surface roughness/hardness tester Fischerscope H-100 (product of Fischer Instruments K.K.), the formed film was measured for elastic power and universal hardness. The results are shown below.

Universal hardness: 249.6 N/mm$^2$

Elastic power: 40.7%

From the data obtained in Examples 3 and 4, it was confirmed that the charge transport layer, which was formed through Diels-Alder reaction from the furan derivative of the present invention and the polyfunctional maleimide compound, was excellent in electrical characteristics and mechanical strength.

Example 5

An under layer coating liquid having the following composition was applied through immersion coating onto an aluminum cylinder having undergone surface polishing (diameter: 60 mm), followed by curing at 60° C. for 15 hours, to thereby form an under layer having a thickness of 3.5 μm.

[Under Layer Coating Liquid]

Compound No. A-8: 4.1 parts

Compound No. B-2: 5.9 parts

Titanium oxide: 50 parts

Tetrahydrofuran: 40 parts

A charge generation layer coating liquid and a charge transport layer coating liquid, each having the following composition, were sequentially applied through immersion coating onto the above-formed under layer, followed by drying, to thereby form a 0.2 μm-thick charge generation layer and a 25 μm-thick charge transport layer. Through the above procedure, an electrophotographic photoconductor was produced.

[Charge Generation Layer Coating Liquid]

Titanylphthalocyanine: 1.5 parts

Polyvinyl butyral (XYHL, product of UCC Co.): 0.5 parts

Cyclohexanone: 200 parts

Methyl ethyl ketone: 80 parts

[Charge Transport Layer Coating Liquid]

Bisphenol Z polycarbonate: 10 parts (PANLITE TS-2050, product of Teijin Chemical Co., Ltd.)

Low-molecular-weight charge transporting compound having the following Structural Formula (D-1): 10 parts Tetrahydrofuran: 100 parts Tetrahydrofuran solution of 1% silicone oil: 0.2 parts (KF50-100CS, product of Shin-Etsu Chemical Co., Ltd.)

BHT: 0.2 parts (D-1)

[chemical structure]

Example 6

An under layer coating liquid having the following composition was applied through immersion coating onto an aluminum cylinder having undergone surface polishing (diameter: 60 mm), followed by curing at 130° C., to thereby form an under layer having a thickness of 3.5 μm.

[chemical structure (F-1)]

[Under Layer Coating Liquid]
  Alkyd resin: 6 parts (BECKOZOLE 1307-60-EL, product of DIC Corporation)
  Melamine resin: 4 parts (SUPER BECKAMINE G-821-60, product of DIC Corporation)
  Titanium oxide: 50 parts
  Methyl ethyl ketone: 50 parts A charge generation layer coating liquid having the following composition was applied through immersion coating onto the formed under layer, followed by drying, to thereby form a charge generation layer having a thickness of 0.2 μm.

[Charge Generation Layer Coating Liquid]
  Titanylphthalocyanine: 1.5 parts
  Polyvinyl butyral (XYHL, product of UCC Co.): 0.5 parts
  Cyclohexanone: 200 parts
  Methyl ethyl ketone: 80 parts In addition, a charge transport layer coating liquid having the following composition was applied through immersion coating onto the formed charge generation layer, followed by curing at 80° C. for 8 hours, to thereby form a charge transport layer having a thickness of 25 μm. Through the above procedure, an electrophotographic photoconductor was produced.

[Charge Transport Layer Coating Liquid]
  Compound No. A-2: 13.4 parts
  Compound No. B-2: 6.6 parts
  Tetrahydrofuran: 70 parts
  Tetrahydrofuran solution of 1% silicone oil: 0.2 parts (KF50-100CS, product of Shin-Etsu Chemical Co., Ltd.)

Example 7

An under layer coating liquid, a charge generation layer coating liquid and a charge transport layer coating liquid, each having the following composition, were sequentially applied onto an aluminum cylinder (diameter: 60 mm), followed by drying, to thereby form a 3.5 μm-thick under layer, a 0.2 μm-thick charge generation layer and a 18 μm-thick charge transport layer.

[Under Layer Coating Liquid]
  Alkyd resin: 6 parts (product of DIC Corporation BECKOZOLE 1307-60-EL)
  Melamine resin: 4 parts (product of DIC Corporation SUPER BECKAMINE G-821-60)
  Titanium oxide: 40 parts
  Methyl ethyl ketone: 50 parts

[Charge Generation Layer Coating Liquid]
  Bisazo pigment having the following Structural Formula (F-1): 2.5 parts
  Polyvinyl butyral (XYHL, product of UCC Co.): 0.5 parts
  Cyclohexanone: 200 parts
  Methyl ethyl ketone: 80 parts

[Charge Transport Layer Coating Liquid]
  Bisphenol Z polycarbonate: 10 parts (PANLITE TS-2050, product of Teijin Chemical Co., Ltd.)
  Low-molecular-weight charge transporting compound (D-1): 7 parts
  Tetrahydrofuran: 100 parts
  Tetrahydrofuran solution of 1% silicone oil: 0.2 parts (KF50-100CS, product of Shin-Etsu Chemical Co., Ltd.)

In addition, a protective layer coating liquid having the following composition was applied through spray coating onto the formed charge transport layer, followed by curing 80° C. for 8 hours, to thereby form a protective layer having a thickness of 5 μm. Through the above procedure, an electrophotographic photoconductor was produced.

[Protective Layer Coating Liquid]
  Compound No. A-2: 13.4 parts
  Compound No. B-2: 6.6 parts
  Tetrahydrofuran: 70 parts
  Tetrahydrofuran solution of 1% silicone oil: 0.2 parts (KF50-100CS, product of Shin-Etsu Chemical Co., Ltd.)

Example 8

Similar to Example 5, a 4 μm-thick under layer was formed on an aluminum cylinder having undergone surface polishing (diameter: 60 mm).

A charge generation layer coating liquid having the following composition was applied through immersion coating onto the formed under layer, followed by drying, to thereby form a charge generation layer having a thickness of 0.2 μm.
[Charge Generation Layer Coating Liquid]
   Titanylphthalocyanine: 1.5 parts
   Polyvinyl butyral (XYHL, product of UCC Co.): 0.5 parts
   Cyclohexanone: 200 parts
   Methyl ethyl ketone: 80 parts
   In addition, a charge transport layer coating liquid having the following composition was applied through immersion coating onto the formed charge generation layer, followed by crosslinking reaction at 80° C. for 10 hours, to thereby obtain an electrophotographic photoconductor.
[Charge Transport Layer Coating Liquid]
   Compound No. A-9: 6.1 parts
   Compound No. B-2: 3.9 parts
   Low-molecular-weight charge transporting compound (D-1): 7 parts
   Tetrahydrofuran: 100 parts
   Tetrahydrofuran solution of 1% silicone oil: 0.2 parts (KF50-100CS, product of Shin-Etsu Chemical Co., Ltd.)
   BHT: 0.2 parts Example 9

A single-layered photosensitive layer coating liquid having the following composition was applied through immersion coating onto an aluminum cylinder (diameter: 60 mm), followed by crosslinking reaction at 90° C. for 20 hours, to thereby form a photosensitive layer having a thickness of 27 μm. Through the above procedure, an electrophotographic photoconductor was produced.
[Single-layered Photosensitive Layer Coating Liquid]
   Charge generating compound having the following Structural Formula (F-2): 5 parts
   Furan derivative obtained in Example 1 (Compound No. 2): 7.1 parts
   Compound No. B-2: 2.9 parts
   Tetrahydrofuran: 30 parts
   Cyclohexanone: 10 parts Example 10

A polyamide resin (CM-8000, product of TORAY INDUSTRIES, INC.) was dissolved in a methanol/butanol solvent mixture. The resultant solution was applied through immersion coating onto an aluminum cylinder (diameter: 60 mm), and naturally dried to form an under layer having a thickness of 0.3 μm. Separately, a bisazo compound having Chemical Formula (F-2) (serving as a charge generating compound) was milled in a cyclohexanone/2-butanone solvent mixture with a ball mill. The resultant dispersion liquid was applied onto the under layer with a doctor blade, and naturally dried to form a charge generation layer having a thickness of 0.3 μm.
   Next, a charge transport layer coating liquid having the following composition was applied through immersion coating onto the formed charge generation layer, and naturally dried. The resultant layer was dried at 130° C. for 30 min to form a charge transport layer having a thickness of 20 μm. Through the above procedure, a photoconductor was produced.
[Charge Transport Layer Coating Liquid]
   Furan derivative obtained in Example 1 (Compound No. 2): 3 parts
   2,2-Di(2-furyl)propane (product of TOKYO CHEMICAL INDUSTRIES Co., Ltd.): 0.9 parts
   Compound No. B-2: 2.4 parts
   Dichloromethane: 25.2 parts Example 11

Similar to Example 10, an under layer and a charge generation layer were formed on an aluminum cylinder having a diameter of 60 mm. Next, a charge transport layer coating liquid having the following composition was applied through immersion coating onto the charge generation layer, and naturally dried. The resultant layer was dried at 80° C. for 8 hours to form a charge transport layer having a thickness of 17 μm. Through the above procedure, a photoconductor was produced.
[Charge Transport Layer Coating Liquid]
   Furan derivative obtained in Example 1 (Compound No. 2); 1.75 parts
   Maleimide derivative; 2.5 parts (copolymer of Compound No. B-8; the ratio of n to m is 80:20 by mole)
   Tetrahydrofuran: 24.1 parts Example 12

An under layer coating liquid, a charge generation layer coating liquid and a charge transport layer coating liquid, each having the following composition, were sequentially applied through immersion coating onto an aluminum cylinder having undergone surface polishing (diameter; 60 mm), followed by drying, to thereby form a 3.5 μm-thick under layer, a 0.2 μm-thick charge generation layer and a 20 μm-thick charge transport layer.
[Under Layer Coating Liquid]
   Alkyd resin; 6 parts (BECKOZOLE 1307-60-EL, product of DIC Corporation)
   Melamine resin; 4 parts (SUPER BECKAMINE G-821-60, product of DIC Corporation)
   Titanium oxide; 50 parts
   Methyl ethyl ketone: 50 parts

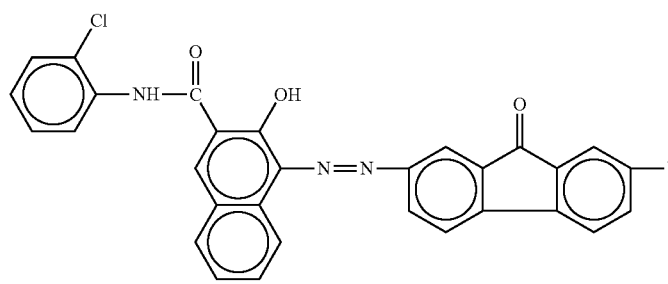
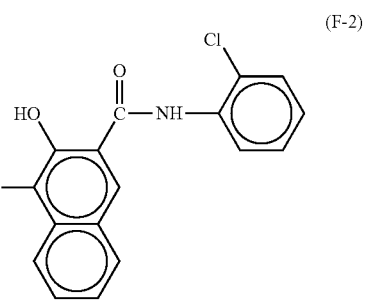

(F-2)

[Charge Generation Layer Coating Liquid]
 Titanylphthalocyanine: 1.5 parts
 Polyvinyl butyral (XYHL, product of UCC Co.): 0.5 parts
 Cyclohexanone: 200 parts
 Methyl ethyl ketone: 80 parts
[Charge Transport Layer Coating Liquid]
 Bisphenol Z polycarbonate: 10 parts (PANLITE TS-2050, product of Teijin Chemical Co., Ltd.)
 Low-molecular-weight charge transporting compound having the following Structural Formula (D-2): 10 parts
 Tetrahydrofuran: 100 parts
 Tetrahydrofuran solution of 1% silicone oil: 0.2 parts (KF50-100CS, product of Shin-Etsu Chemical Co., Ltd.)
 BHT: 0.2 parts coating onto an aluminum cylinder having a diameter of 60 mm, followed by drying at 120° C. for 20 min, to thereby form a photosensitive layer having a thickness of 23 μm.

[Single-layered Photosensitive Layer Coating Liquid]
 3% by mass titanylphthalocyanine dispersion liquid: 6.67 parts (solvent: cyclohexanone, dispersion: vibration mill, 1 hour)
 Low-molecular-weight charge transporting compound (D-1): 6 parts
 Low-molecular-weight charge transporting compound (D-3) having the following Structural Formula (D-3): 4 parts

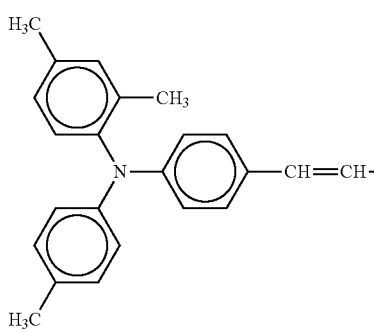

(D-2)

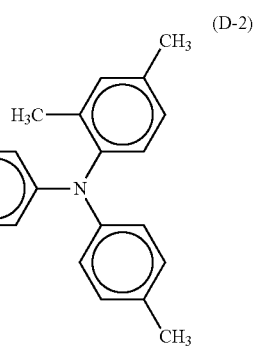

A protective layer coating liquid having the following composition was applied through spray coating onto the formed charge transport layer, followed by crosslinking reaction at 85° C. for 10 hours, to thereby form protective layer having a Bisphenol Z polycarbonate: 10 parts (PANLITE TS-2050, product of Teijin Chemical Co., Ltd.)

Tetrahydrofuran: 74 parts

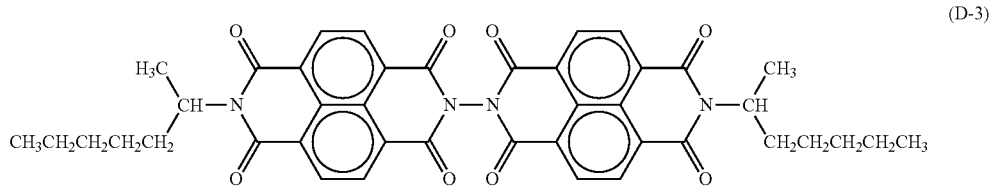

(D-3)

thickness of 5 μm. Through the above procedure, an electrophotographic photoconductor was produced.

[Protective Layer Coating Liquid]

Furan derivative obtained in Example 1 (Compound No. 2): 3 parts 2,2-Di(2-furyl)propane (product of TOKYO CHEMICAL INDUSTRIES Co., Ltd.): 0.9 parts Compound No. B-2: 2.4 parts Tetrahydrofuran: 56.7 parts Example 13

A single-layered photosensitive layer coating liquid having the following composition was applied through immersion Next, a protective layer coating liquid having the following composition was applied through spray coating onto the formed single-layered photosensitive layer, and naturally dried. The resultant layer was dried at 90° C. for 5 hours to form a protective layer having a thickness of 6 μm. Through the above procedure, a photoconductor was produced.
[Protective Layer Coating Liquid]
 Furan derivative obtained in Example 1 (Compound No. 2): 3 parts
 2,2-Di(2-furyl)propane (product of TOKYO CHEMICAL INDUSTRIES Co., Ltd.): 0.9 parts
 Compound No. B-2: 2.4 parts
 Tetrahydrofuran: 56.7 parts Example 14

Similar to Example 5, a 4 μm-thick under layer was formed on an aluminum cylinder having undergone surface polishing (diameter: 60 mm).
A charge generation layer coating liquid having the following composition was applied through immersion coating onto the formed under layer, followed by drying, to thereby form a charge generation layer having a thickness of 0.2 μm.
[Charge Generation Layer Coating Liquid]
Titanylphthalocyanine: 1.5 parts
Polyvinyl butyral (XYHL, product of UCC Co.): 0.5 parts
Cyclohexanone: 200 parts
Methyl ethyl ketone: 80 parts In addition, a charge transport layer coating liquid having the following composition was applied through immersion coating onto the formed charge generation layer, followed by drying, to thereby form a charge transport layer having a thickness of 21 μm.
[Charge Transport Layer Coating Liquid]
Bisphenol Z polycarbonate: 10 parts (PANLITE TS-2050, product of Teijin Chemical Co., Ltd.)
Low-molecular-weight charge transporting compound (D-1): 7 parts
Tetrahydrofuran: 100 parts
Tetrahydrofuran solution of 1% silicone oil: 0.2 parts (KF50-100CS, product of Shin-Etsu Chemical Co., Ltd.)

Furthermore, a protective layer coating liquid having the following composition was applied through spray coating onto the charge transport layer, followed by crosslinking reaction at 85° C. for 10 hours, to thereby form a protective layer having a thickness of 5 μm. Through the above procedure, an electrophotographic photoconductor of the present invention was produced.
[Protective Layer Coating Liquid]
Furan derivative obtained in Example 1 (Compound No. 2): 3 parts
2,2-Di(2-furyl)propane (product of TOKYO CHEMICAL INDUSTRIES Co., Ltd.): 0.9 parts
Compound No. B-2: 2.4 parts
Tetrahydrofuran: 56.7 parts Comparative Example 1

An under layer coating liquid, a charge generation layer coating liquid and a charge transport layer coating liquid, each having the following composition, were sequentially applied through immersion coating onto an aluminum cylinder having undergone surface polishing (diameter: 60 mm), followed by drying, to thereby form a 3.5 μm-thick under layer, a 0.2 μm-thick charge generation layer and a 20 μm-thick charge transport layer. A protective layer coating liquid having the following composition was applied through spray coating onto the formed charge transport layer, and naturally dried for 20 min. Thereafter, the coated film was cured through light irradiation with a metal halide lamp (160 W/cm) under the conditions: irradiation distance: 120 mm, irradiation intensity: 500 mW/cm$^2$ and irradiation time: 180 sec. Furthermore, the resultant layer was dried at 130° C. for 30 min to form a protective layer having a thickness of 4.0 μm. Through the above procedure, an electrophotographic photoconductor was produced.
[Under Layer Coating Liquid]
Alkyd resin: 6 parts (BECKOZOLE 1307-60-EL, product of DIC Corporation)
Melamine resin: 4 parts (SUPER BECKAMINE G-821-60, product of DIC Corporation)
Titanium oxide: 50 parts
Methyl ethyl ketone: 50 parts
[Charge Generation Layer Coating Liquid]
Titanylphthalocyanine: 1.5 parts
Polyvinyl butyral (XYHL, product of UCC Co.): 0.5 parts
Cyclohexanone: 200 parts
Methyl ethyl ketone: 80 parts

[Charge Transport Layer Coating Liquid]
Bisphenol Z polycarbonate: 10 parts (PANLITE TS-2050, product of Teijin Chemical Co., Ltd.)
Low-molecular-weight charge transporting compound (D-2): 10 parts
Tetrahydrofuran: 100 parts
Tetrahydrofuran solution of 1% silicone oil: 0.2 parts (KF50-100CS, product of Shin-Etsu Chemical Co., Ltd.)
BHT: 0.2 parts
[Protective Layer Coating Liquid]
The following charge non-transporting polyfunctional radical polymerizable monomer: 10 parts trimethylolpropane triacrylate (KAYARAD TMPTA, product of NIPPON KAYAKU Co., Ltd.) (molecular weight: 296, the number of functional groups: 3, molecular weight/the number of functional groups=99)
Radical polymerizable charge transporting compound having the following Structural Formula (D-4): 10 parts
Photopolymerization initiator: 1 part (1-hydroxy-cyclohexyl-phenyl-ketone (Irgacure 184, product of Ciba Specialty Chemicals Inc.))
Tetrahydrofuran: 100 parts

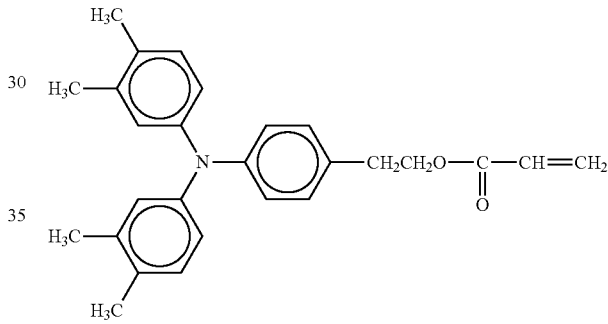

(D-4)

Comparative Example 2

An under layer coating liquid, a charge generation layer coating liquid and a charge transport layer coating liquid, each having the following composition, were sequentially applied through immersion coating onto an aluminum cylinder having undergone surface polishing (diameter: 60 mm), followed by drying, to thereby form a 3.5 μm-thick under layer, a 0.2 μm-thick charge generation layer and a 20 μm-thick charge transport layer.
[Under Layer Coating Liquid]
Alkyd resin: 6 parts (BECKOZOLE 1307-60-EL, product of DIC Corporation)
Melamine resin: 4 parts (SUPER BECKAMINE G-821-60, product of DIC Corporation)
Titanium oxide: 50 parts
Methyl ethyl ketone: 50 parts
[Charge Generation Layer Coating Liquid]
Titanylphthalocyanine: 1.5 parts
Polyvinyl butyral (XYHL, product of UCC Co.): 0.5 parts
Cyclohexanone: 200 parts
Methyl ethyl ketone: 80 parts
[Charge Transport Layer Coating Liquid]
Bisphenol Z polycarbonate: 10 parts (PANLITE TS-2050, product of Teijin Chemical Co., Ltd.)

Low-molecular-weight charge transporting compound (D-1): 10 parts

Tetrahydrofuran: 100 parts

Tetrahydrofuran solution of 1% silicone oil: 0.2 parts (KF50-100CS, product of Shin-Etsu Chemical Co., Ltd.)

BHT: 0.2 parts

A protective layer coating liquid having the following composition was applied through spray coating onto the formed charge transport layer, followed by curing at 150° C. for 30 min, to thereby form a protective layer having a thickness of 5 μm. Through the above procedure, an electrophotographic photoconductor was produced.

[Protective Layer Coating Liquid]

Polyol LZR-170 (product of Fujikura Kasei Co., Ltd., OH equivalent: 367.1): 5 parts Isocyanate: 5 parts (SHT (product of Sumitomo Bayer Urethane, Co., Ltd., NCO equivalent: 212.67))

Conductive filler (zinc antimonate microparticles): 5.1 parts (CELNAX CX-Z210-F (product of NISSAN CHEMICAL INDUSTRIES LTD.))

Low-molecular-weight charge transporting compound (D-1): 7 parts

Tetrahydrofuran: 154.7 parts

Cyclohexanone: 44.2 parts

Comparative Example 3

Similar to Comparative Example 2, a 3.5 μm-thick under layer, a 0.2 μm-thick charge generation layer and a 20 μm-thick charge transport layer were formed on an aluminum cylinder having undergone surface polishing (diameter: 60 mm).

A protective layer coating liquid having the following composition was applied through ring coating onto the charge transport layer, followed by curing at 150° C. for 30 min, to thereby form a protective layer having a thickness of 3 μm. Through the above procedure, an electrophotographic photoconductor was produced.

[Protective Layer Coating Liquid]

Hydroxyl group-containing charge transporting compound having the following Structural Formula (D-5): 4 parts Solution of methyltrimethoxysilane hydrolyzate: 10 parts (which was prepared as follows: 1% aqueous acetic acid solution (1.4 parts) was added dropwise to methyltrimethoxysilane (7 parts), followed by hydrolyzing at 25° C. for 4 hours under stirring)

Tris(2,4-pentandionato)aluminum(III): 0.5 parts

Ethanol: 56 parts

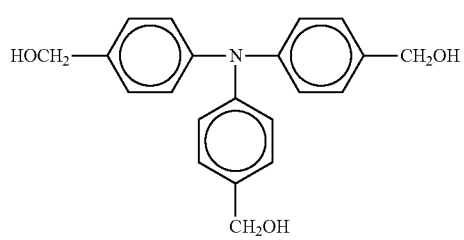

(D-5)

Comparative Example 4

Similar to Example 6, a 3.5 μm-thick under layer was formed on an aluminum cylinder having undergone surface polishing (diameter: 60 mm). And, similar to Example 7, a 0.2 μm-thick charge generation layer and a 25 μm-thick charge transport layer were formed on the under layer, whereby an electrophotographic photoconductor was produced.

Comparative Example 5

Similar to Example 6, a 3.5 μm-thick under layer and a 0.2 μm-thick charge generation layer were formed.

A charge transport layer coating liquid having the following composition was applied through immersion coating onto the formed under layer, followed by curing at 130° C. for 1 hour, to thereby form a charge transport layer having a thickness of 25 μm. Through the above procedure, an electrophotographic photoconductor was produced.

[Charge Transport Layer Coating Liquid]

Hydroxyl group-containing charge transporting compound having the following Structural Formula (D-6): 5 parts Toylene diisocyanate: 5 parts Tetrahydrofuran: 50 parts

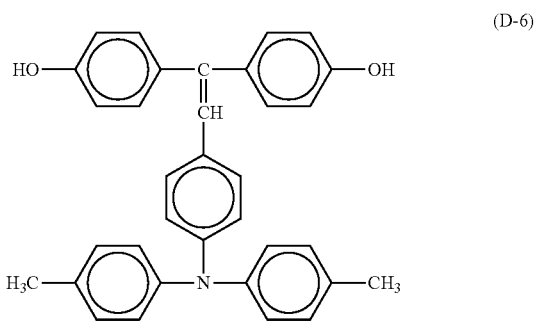

(D-6)

Comparative Example 6

A single-layered photosensitive layer coating liquid having the following composition was applied through immersion coating onto an aluminum cylinder having a diameter of 60 mm, followed by crosslinking reaction at 130° C. for 2 hours, to thereby form a photosensitive layer having a thickness of 27 μm. Through the above procedure, an electrophotographic photoconductor was produced.

[Single-layered Photosensitive Layer Coating Liquid]

Charge generating compound (F-2): 5 parts

Charge transporting compound (D-6): 5 parts

Isocyanate Colonate L (product of NIPPON POLYURETHANE INDUSTRY CO., LTD.): 5 parts Tetrahydrofuran: 60 parts <Evaluation of Photoconductor Characteristics>

Each of the produced electrophotographic photoconductors was mounted to a process cartridge of a digital full-color complex machine MP C7500 SP (product of Ricoh Co., Ltd.), and then the process cartridge was mounted to the main body. The machine was caused to print A4 paper sheets (My Recycle Paper GP, product of Ricoh Co., Ltd.) at a pixel density of 600×600 dpi. Specifically, 10 paper sheets with a test pattern of halftone belt for yellow, magenta, cyan or black were consecutively printed out at a printing speed of 60 sheets/min. As a result, each electrophotographic photoconductor was evaluated based on the obtained image according to the following criteria:

A: A clear image was formed;

B: A partially abnormal image was formed; and

C: A considerably bad image was formed.

Also, the electrophotographic photoconductors were evaluated for abrasion amount after printing of 10,000 paper sheets (some electrophotographic photoconductors could not print out 10,000 paper sheets). The results are shown in Table 3.

<Evaluation of Recycling Property>

Each of the produced electrophotographic photoconductors was placed in a drying apparatus set to 130° C. for 5 min. Immediately after drying, the electrophotographic photoconductor was immersed in tetrahydrofuran, and the photosensitive layer was dissolved therein through the application of ultrasonic wave for 5 min. Whether or not the crosslinked film layer was removed was visually confirmed. The results are shown in Table 3.

TABLE 3

| | Evaluation of printed image | Abrasion amount (μm) | Recycling property |
|---|---|---|---|
| Ex. 5 | A | 1.0 | All the layers removed |
| Ex. 6 | A | 0.4 | Only the under layer remained |
| Ex. 7 | A | 0.4 | Only the under layer remained |
| Ex. 8 | A | 0.5 | All the layers removed |
| Ex. 9 | A | 0.6 | All the layers removed |
| Ex. 10 | A | 0.2 | All the layers removed |
| Ex. 11 | A | 0.4 | All the layers removed |
| Ex. 12 | A | 0.2 | Only the under layer remained |
| Ex. 13 | A | 0.2 | All the layers removed |
| Ex. 14 | A | 0.2 | All the layers removed |
| Comp. Ex. 1 | A | 0.1 | The protective layer not dissolved |
| Comp. Ex. 2 | A | 0.2 | The protective layer not dissolved |
| Comp. Ex. 3 | A | 0.2 | The protective layer not dissolved |
| Comp. Ex. 4 | A | 1.0 | Only the under layer remained |
| Comp. Ex. 5 | C | Not evaluated | The charge transport layer not dissolved |
| Comp. Ex. 6 | C | Not evaluated | The photosensitive layer not dissolved |

INDUSTRIAL APPLICABILITY

The furan derivative of the present invention has both reactivity and charge transportability (hole transportability), and can form through Diels-Alder reaction a thermoplastic resin or crosslinked cured resin. The obtained resin shows charge transportability, and thus, is useful for semiconductor materials for organic devices such as organic EL elements, organic electrophotographic photoconductors, organic TFTs and organic solar cells.

The electrophotographic photoconductor of the present invention has a long service life and has a conductive support which can be easily recycled. Thus, the electrophotographic photoconductor can be widely used in, for example, laser printers, direct digital platemakers, full-color copiers employing a direct or indirect electrophotographic multicolor image developing method, full-color laser printers, CRT printers, LED printers, liquid crystal printers, laser platemakers and full-color plain paper facsimiles.

The invention claimed is:

1. An electrophotographic photoconductor comprising:
a structure three-dimensionally crosslinked through Diels-Alder reaction,
a conductive support, and
a photosensitive layer containing one or more layers,
at least the photosensitive layer being provided over the conductive support,
wherein the one or more layers are a charge generation layer and a charge transport layer, wherein at least an under layer the charge generation layer and the charge transort layer are laminated in this order on the conductive support, and wherein the charge transport layer comprises the structure three-dimensionally crosslinked through Diels-Alder reaction,
wherein the structure three-dimensionally crosslinked through Diels-Alder reaction is formed through Diels-Alder reaction between a furan derivative serving as a diene and a maleimide derivative serving as a dienophile, and
wherein the furan derivative is represented by the following General Formula (1):

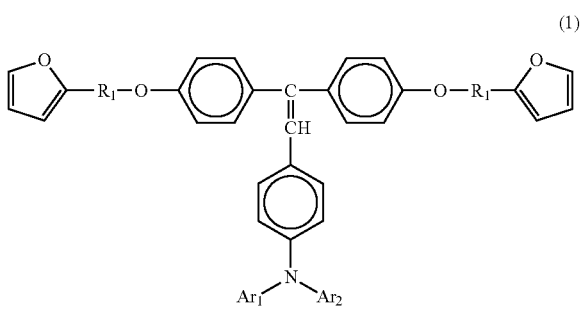

(1)

where $Ar_1$ and $Ar_2$ each independently represent an aryl group which may have a substituent and $R_1$ represents a C1-C6 alkylene group.

2. The electrophotographic photoconductor according to claim 1, wherein the furan derivative is represented by the following General Formula (2):

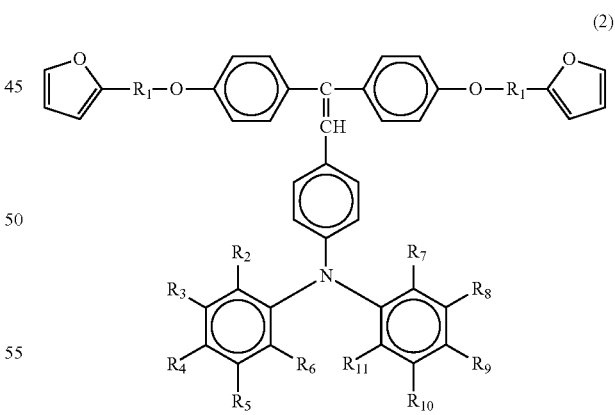

(2)

where $R_1$ represents a C1-C6 alkylene group, $R_2$ to $R_{11}$ each independently represent a C1-C6 alkyl group which may have a substituent, a C1-C6 alkoxy group which may have a substituent, or an aryl group which may have a substituent.

3. The electrophotographic photoconductor according to claim 2, wherein the furan derivative is represented by the following General Formula (3):

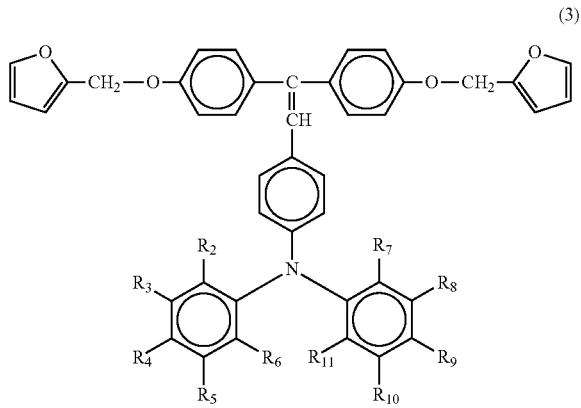

where $R_2$ to $R_{11}$ each independently represent a C1-C6 alkyl group which may have a substituent, a C1-C6 alkoxy group which may have a substituent, or an aryl group which may have a substituent.

4. An electrophotographic photoconductor comprising:
a structure three-dimensionally crosslinked through Diels-Alder reaction,
a conductive support, and
a photosensitive layer containing one or more layers,
at least the photosensitive layer being provided over the conductive support,
wherein the one or more layers are a charge generation layer and a charge transport layer,
wherein at least an under layer, the charge generation layer, the charge transport layer and a protective layer are laminated in this order on the conductive support, and
wherein the protective layer comprises the structure three-dimensionally crosslinked through Diels-Alder reaction,
wherein the structure three-dimensionally crosslinked through Diels-Alder reaction is formed through Diels-Alder reaction between a furan derivative serving as a diene and a maleimide derivative serving as a dienophile, and
wherein the furan derivative is represented by the following General Formula (1):

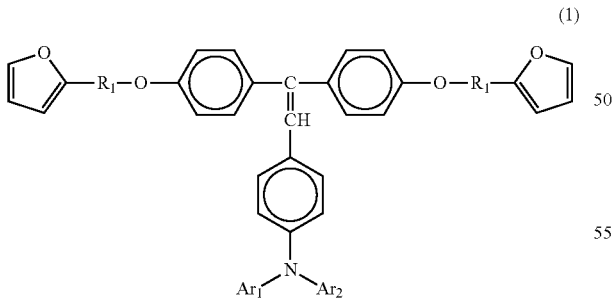

where $Ar_1$ and $Ar_2$ each independently represent an aryl group which may have a substituent, and $R_1$ represents a C1-C6 alkylene group.

5. The electrophotographic photoconductor according to claim 4, wherein the furan derivative is represented by the following General Formula (2):

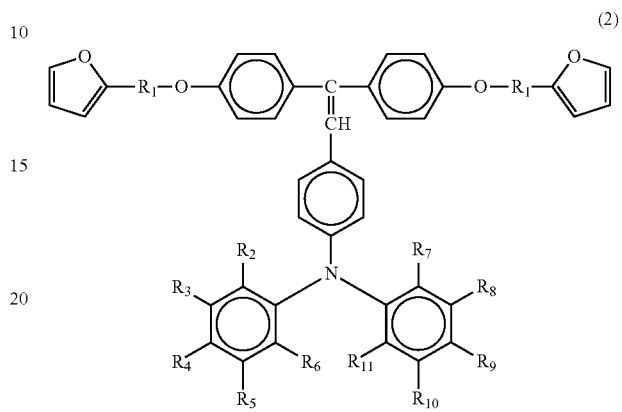

where $R_1$ represents a C1-C6 alkylene group, $R_2$ to $R_{11}$ each independently represent a C1-C6 alkyl group which may have a substituent, a C1-C6 alkoxy group which may have a substituent, or an aryl group which may have a substituent.

6. The electrophotographic photoconductor according to claim 5, wherein the furan derivative is represented by the following General Formula (3):

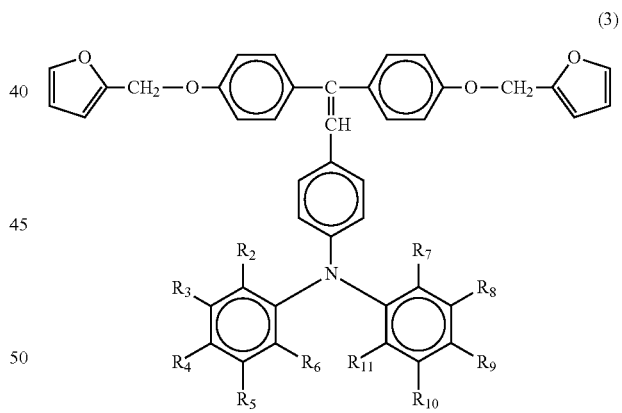

where $R_2$ to $R_{11}$ each independently represent a C1-C6 alkyl group which may have a substituent, a C1-C6 alkoxy group which may have a substituent, or an aryl group which may have a substituent.

* * * * *